(12) United States Patent
Sakamuri et al.

(10) Patent No.: US 11,597,744 B2
(45) Date of Patent: Mar. 7, 2023

(54) CHIRAL PHOSPHORAMIDITE AUXILIARIES AND METHODS OF THEIR USE

(71) Applicant: Sirius Therapeutics, Inc., Boston, MA (US)

(72) Inventors: Sukumar Sakamuri, San Diego, CA (US); Curt W. Bradshaw, San Diego, CA (US); Dingguo Liu, San Diego, CA (US); Laxman Eltepu, San Diego, CA (US)

(73) Assignee: SIRIUS THERAPEUTICS, INC., Cambridge, MA (US)

( * ) Notice: Subject to any disclaimer, the term of this patent is extended or adjusted under 35 U.S.C. 154(b) by 125 days.

(21) Appl. No.: 16/627,091

(22) PCT Filed: Jul. 2, 2018

(86) PCT No.: PCT/US2018/040592
§ 371 (c)(1),
(2) Date: Dec. 27, 2019

(87) PCT Pub. No.: WO2019/006455
PCT Pub. Date: Jan. 3, 2019

(65) Prior Publication Data
US 2020/0140476 A1  May 7, 2020

Related U.S. Application Data

(60) Provisional application No. 62/527,078, filed on Jun. 30, 2017.

(51) Int. Cl.
*C07H 19/11* (2006.01)
*C07H 19/213* (2006.01)
*C07H 21/04* (2006.01)

(52) U.S. Cl.
CPC .......... *C07H 19/11* (2013.01); *C07H 19/213* (2013.01); *C07H 21/04* (2013.01)

(58) Field of Classification Search
CPC ....... C07H 19/11; C07H 19/213; C07H 21/04
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,500,707 A | 2/1985 | Caruthers et al. |
| 4,517,338 A | 5/1985 | Urdea et al. |
| 4,659,774 A | 4/1987 | Webb et al. |
| 4,668,777 A | 5/1987 | Caruthers et al. |
| 4,672,110 A | 6/1987 | Letsinger |
| 4,711,955 A | 12/1987 | Ward et al. |
| 4,725,677 A | 2/1988 | Koster et al. |
| 4,751,180 A | 6/1988 | Cousens et al. |
| 4,806,463 A | 2/1989 | Goodchild et al. |
| 4,845,205 A | 7/1989 | Huynh Dinh et al. |
| 4,877,805 A | 10/1989 | Kligman |
| 4,935,233 A | 6/1990 | Bell et al. |
| 4,973,679 A | 11/1990 | Caruthers et al. |
| 4,975,282 A | 12/1990 | Cullis et al. |
| 4,980,378 A | 12/1990 | Wong et al. |
| 4,994,213 A | 2/1991 | Aitcheson et al. |
| 5,000,307 A | 3/1991 | Bruke |
| 5,000,958 A | 3/1991 | Fountain et al. |
| 5,023,087 A | 6/1991 | Yau-Young |
| 5,032,582 A | 7/1991 | Abra |

(Continued)

FOREIGN PATENT DOCUMENTS

| | | |
|---|---|---|
| CA | 2252144 A1 | 4/2000 |
| CA | 2929651 A1 | 5/2015 |
| CN | 1079473 A | 12/1993 |
| CN | 102459302 A | 5/2012 |
| DE | 2847064 A1 | 5/1980 |
| DE | 102005039726 B3 | 1/2007 |
| EP | 0586106 A1 | 3/1994 |
| EP | 1447412 A1 | 8/2004 |
| FR | 2834465 A1 | 7/2003 |
| JP | H05-505941 A | 9/1993 |

(Continued)

OTHER PUBLICATIONS

U.S. Appl. No. 16/780,204, Bradshaw et al.
Abramova et al., "Synthesis and properties of photolabile (caged) phosphotriester derivatives of dinucleoside phosphates," Russian J Bioorg Chem. 26(3):174-82 (2000).

(Continued)

*Primary Examiner* — Layla D Berry
(74) *Attorney, Agent, or Firm* — Wilson Sonsini Goodrich & Rosati

(57) ABSTRACT

Disclosed are chiral phosphoramidite auxiliary compositions for diastereoselective synthesis of stereochemically enriched oligonucleotides, and nucleoside phosphoramidite compounds comprising the same. Exemplary structures of the chiral phosphoramidite auxiliary compositions include Formulas (IA) and (IB).

(IA)

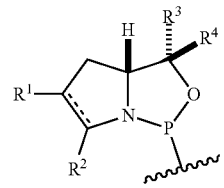

(IB)

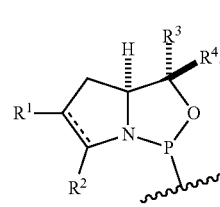

20 Claims, No Drawings

(56) References Cited

U.S. PATENT DOCUMENTS

| | | |
|---|---|---|
| 5,049,388 A | 9/1991 | Knight et al. |
| 5,082,866 A | 1/1992 | Wong et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,153,319 A | 10/1992 | Caruthers et al. |
| 5,169,637 A | 12/1992 | Lenk et al. |
| 5,175,273 A | 12/1992 | Bischofberger et al. |
| 5,194,266 A | 3/1993 | Abra et al. |
| 5,218,103 A | 6/1993 | Caruthers et al. |
| 5,268,464 A | 12/1993 | Brill |
| 5,278,302 A | 1/1994 | Caruthers et al. |
| 5,319,079 A | 6/1994 | Reddy et al. |
| 5,356,633 A | 10/1994 | Woodle et al. |
| 5,367,066 A | 11/1994 | Urdea et al. |
| 5,409,704 A | 4/1995 | Bally et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,155 A | 9/1996 | Bailey et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,670,617 A | 9/1997 | Frankel et al. |
| 5,677,441 A | 10/1997 | Waldman et al. |
| 5,681,941 A | 10/1997 | Cook et al. |
| 5,688,525 A | 11/1997 | Adler-Moore et al. |
| 5,696,251 A | 12/1997 | Arnold, Jr. et al. |
| 5,733,523 A | 3/1998 | Kuijpers et al. |
| 5,760,209 A | 6/1998 | Cheruvallath et al. |
| 5,770,713 A | 6/1998 | Imbach et al. |
| 5,770,725 A | 6/1998 | Gosselin et al. |
| 5,789,562 A | 8/1998 | Seela et al. |
| 5,849,905 A | 12/1998 | Gosselin et al. |
| 5,874,104 A | 2/1999 | Adler-Moore et al. |
| 5,874,552 A | 2/1999 | Jones et al. |
| 5,902,879 A | 5/1999 | Polouchine |
| 5,936,077 A | 8/1999 | Pfleiderer et al. |
| 5,955,591 A | 9/1999 | Imbach et al. |
| 5,959,099 A | 9/1999 | Cheruvallath et al. |
| 5,968,506 A | 10/1999 | Weinrich et al. |
| 6,022,735 A | 2/2000 | Curiel et al. |
| 6,030,955 A | 2/2000 | Stein et al. |
| 6,077,663 A | 6/2000 | Curiel et al. |
| 6,118,020 A | 9/2000 | Buyuktimkin et al. |
| 6,124,445 A | 9/2000 | Imbach et al. |
| 6,221,355 B1 | 4/2001 | Dowdy |
| 6,316,003 B1 | 11/2001 | Frankel et al. |
| 6,326,358 B1 | 12/2001 | Manoharan |
| 6,326,478 B1 | 12/2001 | Cheruvallath et al. |
| 6,376,248 B1 | 4/2002 | Hawley-Nelson et al. |
| 6,399,756 B1 | 6/2002 | Cheruvallath et al. |
| 6,420,546 B1 | 7/2002 | Seliger et al. |
| 6,468,986 B1 | 10/2002 | Zuckermann et al. |
| 6,521,775 B2 | 2/2003 | Cheruvallath et al. |
| 6,531,590 B1 | 3/2003 | Manoharan et al. |
| 6,559,279 B1 | 5/2003 | Manoharan et al. |
| 6,610,837 B1 | 8/2003 | Guzaev et al. |
| 6,610,841 B1 | 8/2003 | Warren |
| 6,613,956 B1 | 9/2003 | Klippel et al. |
| 6,645,501 B2 | 11/2003 | Dowdy |
| 6,677,471 B2 | 1/2004 | Cheruvallath et al. |
| 6,747,142 B1 | 6/2004 | Polouchine |
| 6,841,535 B2 | 1/2005 | Divita et al. |
| 6,900,301 B2 | 5/2005 | Cook et al. |
| 6,900,540 B1 | 5/2005 | Teig et al. |
| 6,903,077 B1 | 6/2005 | Heintz |
| 6,906,182 B2 | 6/2005 | Ts'o et al. |
| 6,919,437 B1 | 7/2005 | Manoharan et al. |
| 7,045,309 B2 | 5/2006 | Johnson et al. |
| 7,084,248 B2 | 8/2006 | Summerton |
| 7,166,692 B2 | 1/2007 | Karas |
| 7,262,177 B2 | 8/2007 | Ts'O et al. |
| 7,420,031 B2 | 9/2008 | Karas |
| 7,491,805 B2 | 2/2009 | Vargeese et al. |
| 7,514,530 B2 | 4/2009 | Divita et al. |
| 7,713,944 B2 | 5/2010 | Kinberger et al. |
| 7,754,944 B2 | 7/2010 | Fu et al. |
| 7,785,610 B2 | 8/2010 | Fearon et al. |
| 7,879,813 B2 | 2/2011 | Chatterton |
| 8,114,973 B2 | 2/2012 | Siddiqi et al. |
| 8,153,361 B1 | 4/2012 | Benner |
| 8,158,770 B2 | 4/2012 | Wedekind et al. |
| 8,450,467 B2 | 5/2013 | Manoharan et al. |
| 8,476,083 B1 | 7/2013 | Algar et al. |
| 8,501,930 B2 | 8/2013 | Rozema et al. |
| 8,507,455 B2 | 8/2013 | Manoharan et al. |
| 8,541,569 B2 | 9/2013 | Srivastava et al. |
| 8,691,971 B2 | 4/2014 | Petersen |
| 8,853,132 B2 * | 10/2014 | Heindl .................. C07F 9/6552 506/9 |
| 8,859,755 B2 * | 10/2014 | Wada ..................... C07H 19/10 536/25.33 |
| 9,950,001 B2 | 4/2018 | Dowdy et al. |
| 2002/0013287 A1 | 1/2002 | Sampath et al. |
| 2003/0105026 A1 | 6/2003 | Kozhemyakin et al. |
| 2003/0143732 A1 | 7/2003 | Fosnaugh et al. |
| 2003/0225016 A1 | 12/2003 | Fearon et al. |
| 2004/0018140 A1 | 1/2004 | Karl et al. |
| 2004/0082774 A1 | 4/2004 | Guzaev et al. |
| 2004/0110205 A1 | 6/2004 | Wang |
| 2004/0116680 A1 | 6/2004 | Beier |
| 2004/0204377 A1 | 10/2004 | Rana |
| 2004/0229839 A1 | 11/2004 | Babu et al. |
| 2005/0042603 A1 | 2/2005 | Wang |
| 2005/0147993 A1 | 7/2005 | Khan |
| 2005/0191687 A1 | 9/2005 | Wang et al. |
| 2005/0239687 A1 | 10/2005 | Divita et al. |
| 2005/0260756 A1 | 11/2005 | Troy et al. |
| 2006/0030003 A1 | 2/2006 | Simon |
| 2006/0035815 A1 | 2/2006 | Chen et al. |
| 2006/0040882 A1 | 2/2006 | Chen et al. |
| 2006/0142232 A1 | 6/2006 | Kinberger et al. |
| 2006/0178297 A1 | 8/2006 | Troy et al. |
| 2006/0182736 A1 | 8/2006 | Kim et al. |
| 2006/0205665 A1 | 9/2006 | Bonny |
| 2006/0222657 A1 | 10/2006 | Dowdy et al. |
| 2006/0228725 A1 | 10/2006 | Salafsky |
| 2006/0275371 A1 | 12/2006 | Dai et al. |
| 2007/0123450 A1 | 5/2007 | Kozhemyakin et al. |
| 2007/0207973 A1 | 9/2007 | Daifuku et al. |
| 2008/0027025 A1 | 1/2008 | Dowdy et al. |
| 2008/0153737 A1 | 6/2008 | Lieberman et al. |
| 2008/0227104 A1 | 9/2008 | Hayashizaki et al. |
| 2009/0012030 A1 | 1/2009 | Chatterton et al. |
| 2009/0093026 A1 | 4/2009 | Dowdy et al. |
| 2009/0093425 A1 | 4/2009 | Dowdy et al. |
| 2009/0098049 A1 | 4/2009 | Dowdy et al. |
| 2009/0203132 A1 | 8/2009 | Swayze et al. |
| 2010/0047164 A1 | 2/2010 | Bigner et al. |
| 2010/0120164 A1 | 5/2010 | Salafsky |
| 2010/0255558 A1 | 10/2010 | Niemeyer et al. |
| 2011/0059180 A1 | 3/2011 | Barthelemy et al. |
| 2011/0137010 A1 | 6/2011 | Srivastava et al. |
| 2011/0312507 A1 | 12/2011 | Liu et al. |
| 2012/0035115 A1 | 2/2012 | Manoharan et al. |
| 2012/0040459 A1 | 2/2012 | Khvorova et al. |
| 2012/0070505 A1 | 3/2012 | Barthelemy et al. |
| 2012/0122235 A1 | 5/2012 | Chase et al. |
| 2012/0122779 A1 | 5/2012 | Kirshenbaum et al. |
| 2012/0142763 A1 | 6/2012 | Dowdy et al. |
| 2012/0316224 A1 | 12/2012 | Verdine et al. |
| 2013/0040823 A1 | 2/2013 | Freskgard et al. |
| 2013/0052731 A1 | 2/2013 | Ma et al. |
| 2013/0066063 A1 | 3/2013 | Berry et al. |
| 2013/0123334 A1 | 5/2013 | Feinstein et al. |
| 2013/0149787 A1 | 6/2013 | Chase et al. |
| 2013/0171242 A1 | 7/2013 | Lim et al. |

(56) References Cited

U.S. PATENT DOCUMENTS

| | | |
|---|---|---|
| 2013/0184450 A1 | 7/2013 | Wada et al. |
| 2014/0045719 A1 | 2/2014 | Heindl et al. |
| 2014/0081012 A1 | 3/2014 | DeSimone et al. |
| 2015/0197540 A1 | 7/2015 | Shimizu et al. |
| 2015/0238516 A1 | 8/2015 | Dowdy et al. |
| 2016/0257961 A1 | 9/2016 | Bradshaw et al. |
| 2017/0114341 A1 | 4/2017 | Bradshaw et al. |
| 2017/0355727 A1 | 12/2017 | Seth et al. |
| 2018/0303864 A1 | 10/2018 | Dowdy et al. |
| 2019/0194655 A1 | 6/2019 | Bradshaw et al. |
| 2019/0202855 A1 | 7/2019 | Sakamuri et al. |
| 2020/0392498 A1 | 12/2020 | Bradshaw et al. |

FOREIGN PATENT DOCUMENTS

| | | |
|---|---|---|
| JP | H10-509740 A | 9/1998 |
| JP | 2000-507928 A | 6/2000 |
| JP | 2004-536027 A | 12/2004 |
| JP | 2004-537535 A | 12/2004 |
| JP | 2005-507928 A | 3/2005 |
| JP | 2010-521657 A | 6/2010 |
| WO | WO-9014226 A1 | 11/1990 |
| WO | WO-91/14696 A1 | 10/1991 |
| WO | WO-93/12131 A1 | 6/1993 |
| WO | WO-93/12132 A1 | 6/1993 |
| WO | WO-93/14108 A1 | 7/1993 |
| WO | WO-93/16094 A2 | 8/1993 |
| WO | WO-93/24510 A1 | 12/1993 |
| WO | WO-94/26761 A1 | 11/1994 |
| WO | WO-94/26764 A1 | 11/1994 |
| WO | WO-95/32980 A1 | 12/1995 |
| WO | WO-96/06105 A1 | 2/1996 |
| WO | WO-96/11010 A1 | 4/1996 |
| WO | WO-96/40061 A1 | 12/1996 |
| WO | WO-97/06183 A1 | 2/1997 |
| WO | WO-97/14708 A1 | 4/1997 |
| WO | WO-97/47637 A1 | 12/1997 |
| WO | WO-98/11121 A1 | 3/1998 |
| WO | WO-98/39290 A1 | 9/1998 |
| WO | WO-98/39349 A1 | 9/1998 |
| WO | WO-98/42722 A1 | 10/1998 |
| WO | WO-99/55717 A1 | 11/1999 |
| WO | WO-00/00499 A1 | 1/2000 |
| WO | WO-00/02896 A1 | 1/2000 |
| WO | WO-00/03720 A1 | 1/2000 |
| WO | WO-OO/11952 A1 | 3/2000 |
| WO | WO-00/23454 A1 | 4/2000 |
| WO | WO-00/40723 A2 | 7/2000 |
| WO | WO-00/47593 A1 | 8/2000 |
| WO | WO-00/50642 A1 | 8/2000 |
| WO | WO-00/55179 A1 | 9/2000 |
| WO | WO-01/16149 A2 | 3/2001 |
| WO | WO-01/49701 A1 | 7/2001 |
| WO | WO-01/60316 A2 | 8/2001 |
| WO | WO-01/72123 A1 | 10/2001 |
| WO | WO-01/72764 A1 | 10/2001 |
| WO | WO-02/04475 A1 | 1/2002 |
| WO | WO-02/18951 A2 | 3/2002 |
| WO | WO-02/20543 A2 | 3/2002 |
| WO | WO-02/20544 A1 | 3/2002 |
| WO | WO-02/43771 A2 | 6/2002 |
| WO | WO-02/079216 A1 | 10/2002 |
| WO | WO-02/081739 A2 | 10/2002 |
| WO | WO-03/000922 A2 | 1/2003 |
| WO | WO-03/004512 A1 | 1/2003 |
| WO | WO-03/019145 A2 | 3/2003 |
| WO | WO-03/039523 A2 | 5/2003 |
| WO | WO-03/042658 A2 | 5/2003 |
| WO | WO-03/059394 A1 | 7/2003 |
| WO | WO-2004/007721 A1 | 1/2004 |
| WO | WO-2004/014312 A2 | 2/2004 |
| WO | WO-2004/028454 A2 | 4/2004 |
| WO | WO-2004/041194 A2 | 5/2004 |
| WO | WO-2004/044232 A1 | 5/2004 |
| WO | WO-2004/048545 A2 | 6/2004 |
| WO | WO-2004/091499 A2 | 10/2004 |
| WO | WO-2005/001143 A2 | 1/2005 |
| WO | WO-2005/019236 A1 | 3/2005 |
| WO | WO-2005/019237 A1 | 3/2005 |
| WO | WO-2005/034732 A2 | 4/2005 |
| WO | WO-2005/047468 A2 | 5/2005 |
| WO | WO-2005/062947 A2 | 7/2005 |
| WO | WO-2005/065150 A2 | 7/2005 |
| WO | WO-2005/084158 A2 | 9/2005 |
| WO | WO-2005/107463 A1 | 11/2005 |
| WO | WO-2005/115410 A2 | 12/2005 |
| WO | WO-2005/115479 A2 | 12/2005 |
| WO | WO-2005/115749 A1 | 12/2005 |
| WO | WO-2005/117991 A2 | 12/2005 |
| WO | WO-2006/000922 A2 | 1/2006 |
| WO | WO-2006/007721 A1 | 1/2006 |
| WO | WO-2006/028601 A2 | 3/2006 |
| WO | WO-2006/073458 A2 | 7/2006 |
| WO | WO-2007/002567 A2 | 1/2007 |
| WO | WO-2007/011946 A2 | 1/2007 |
| WO | WO-2007/070947 A1 | 6/2007 |
| WO | WO-2007/091269 A2 | 8/2007 |
| WO | WO-2007/125429 A2 | 11/2007 |
| WO | WO-2008/016906 A2 | 2/2008 |
| WO | WO-2008/120016 A1 | 10/2008 |
| WO | WO-2008/124150 A1 | 10/2008 |
| WO | WO-2009/017861 A2 | 2/2009 |
| WO | WO-2009/018332 A1 | 2/2009 |
| WO | WO-2009/089425 A1 | 7/2009 |
| WO | WO-2009/129120 A2 | 10/2009 |
| WO | WO-2009/144481 A2 | 12/2009 |
| WO | WO-2010/027512 A2 | 3/2010 |
| WO | WO-2010/039543 A2 | 4/2010 |
| WO | WO-2010/039548 A2 | 4/2010 |
| WO | WO-2010/048549 A2 | 4/2010 |
| WO | WO-2010/081114 A2 | 7/2010 |
| WO | WO-2010/090723 A2 | 8/2010 |
| WO | WO-2010/129853 A2 | 11/2010 |
| WO | WO-2010/135520 A1 | 11/2010 |
| WO | WO-2010/147831 A1 | 12/2010 |
| WO | WO-2011/002200 A2 | 1/2011 |
| WO | WO-2011/003018 A2 | 1/2011 |
| WO | WO-2011/005761 A1 | 1/2011 |
| WO | WO-2011/005860 A2 | 1/2011 |
| WO | WO-2011/015521 A1 | 2/2011 |
| WO | WO-2011/037731 A1 | 3/2011 |
| WO | WO-2011/038031 A1 | 3/2011 |
| WO | WO-2011/038158 A2 | 3/2011 |
| WO | WO-2011/076923 A1 | 6/2011 |
| WO | WO-2011/090793 A2 | 7/2011 |
| WO | WO-2011/103468 A2 | 8/2011 |
| WO | WO-2011/128374 A1 | 10/2011 |
| WO | WO-2011/133871 A2 | 10/2011 |
| WO | WO-2011/139695 A1 | 11/2011 |
| WO | WO-2011/139699 A2 | 11/2011 |
| WO | WO-2011/139911 A2 | 11/2011 |
| WO | WO-2012/030626 A2 | 3/2012 |
| WO | WO-2012/045075 A1 | 4/2012 |
| WO | WO-2012/051492 A2 | 4/2012 |
| WO | WO-2012/061719 A2 | 5/2012 |
| WO | WO-2012/068340 A2 | 5/2012 |
| WO | WO-2012/091091 A1 | 7/2012 |
| WO | WO-2012/094343 A1 | 7/2012 |
| WO | WO-2012/177949 A2 | 12/2012 |
| WO | WO-2013/012758 A2 | 1/2013 |
| WO | WO-2013/013068 A2 | 1/2013 |
| WO | WO-2013/022967 A1 | 2/2013 |
| WO | WO-2013/040429 A1 | 3/2013 |
| WO | WO-2013/045939 A1 | 4/2013 |
| WO | WO-2013/110902 A1 | 8/2013 |
| WO | WO-2013/126034 A1 | 8/2013 |
| WO | WO-2014/012081 A2 | 1/2014 |
| WO | WO-2014/031575 A1 | 2/2014 |
| WO | WO-2015069932 A1 | 5/2015 |
| WO | WO-2015/168589 A2 | 11/2015 |
| WO | WO-2015188197 A2 | 12/2015 |
| WO | WO-2016/094677 A2 | 6/2016 |
| WO | WO-2017100461 A1 | 6/2017 |

(56) References Cited

FOREIGN PATENT DOCUMENTS

| WO | WO-2018035380 A1 | 2/2018 |
|---|---|---|
| WO | WO-2018/237194 A1 | 12/2018 |
| WO | WO-2019006455 A1 | 1/2019 |

OTHER PUBLICATIONS

Abu-Amer et al., "TAT fusion proteins containing tyrosine 42-deleted IkappaBalpha arrest osteoclastogenesis," J Biol Chem. 276(32):30499-503 (2001).
Alvarez et al., "Photocleavable protecting groups as nucleobase protections allowed the solid-phase synthesis of base-sensitive SATE-prooligonucleotides," J Org Chem. 64(17):6319-28 (1999).
Astriab-Fisher et al., "Conjugates of antisense oligonucleotides with the Tat and antennapedia cell-penetrating peptides: effects on cellular uptake, binding to target sequences, and biologic actions," Pharm Res. 19(6):744-54 (2002).
Barquinero et al., "Retroviral vectors: new applications for an old tool," Gene Ther. 11 (Suppl 1):S3-9 (2004).
Beaucage et al., "Advances in the synthesis of oligonucleotides by the phosphoramidite approach," Tetrahedron. 48(12): 2223-311 (1992).
Beaucage et al., "Deoxynucleoside phosphoramidites—a new class of key intermediates for deoxypolynucleotide synthesis," Tetrahedron Lett. 22(20):1859-62 (1981).
Beaucage et al., "The synthesis of modified oligonucleotides by the phosphoramidite approach and their applications," Tetrahedron. 49(28):6123-94 (1993).
Behlke, "Progress towards in vivo use of siRNAs," Mol Ther. 13(4):644-70 (2006).
Bernstein et al., "The rest is silence," RNA. 7(11):1509-21 (2001).
Bologna et al., "The prooligonucleotide approach: synthesis of mixed phosphodiester and SATE phosphotriester prooligonucleotides using H-phosphonate and phosphoramidite chemistries," Eur J Org Chem. 2353-8(1999).
Breslow et al., "Recognition and catalysis in nucleic acid chemistry," Proc Natl Acad Sci USA. 90(4):1201-7 (1993).
Brugidou et al., "The retro-inverso form of a homeobox-derived short peptide is rapidly internalised by cultured neurones: a new basis for an efficient intracellular delivery system," Biochem Biophys Res Commun. 214(2):685-93 (1995).
Chauhan et al., "PTD-fusion peptide as a delivery vehicle for siRNA to target HIV reservoirs," Mol Ther. 13(1):S277 (2006).
Chen et al., "Lipophilic siRNAs mediate efficient gene silencing in oligodendrocytes with direct CNS delivery," J Control Release. 144(2): 227-32 (2010).
Chorev et al., "Recent developments in retro peptides and proteins—an ongoing topochemical exploration," Trends Biotechnol. 13(10):438-45 (1995).
Dias et al., "DNA-lipid systems. A physical chemistry study," Braz J Med Biol Res. 35(5):509-22 (2002).
Dominska et al., "Breaking down the barriers: siRNA delivery and endosome escape," J Cell Sci. 123(Pt 8):1183-9 (2010).
Eguchi et al., "Protein transduction domain of HIV-1 Tat protein promotes efficient delivery of DNA into mammalian cells," J Biol Chem. 276(28):26204-10 (2001).
El-Sagheer et al., "Synthesis of alkyne- and azide-modified oligonucleotides and their cyclization by the CuAAC (click) reaction," Curr Protoc Nucleic Acid Chem. Chapter 4:Unit 4.33, 35(1):4.33.1-4.33.21 (2008) (21 pages).
Elliott et al., "Intercellular trafficking and protein delivery by a herpesvirus structural protein," Cell. 88(2):223-33 (1997).
Explore the Power of Polyacrylamide [online]. Hydrosorb, Inc. 2002 [retrieved on Mar. 10, 2015] from URL <http://aquaben.com/wp-content/uploads/2013/06/powerofpolyacrylamide.pdf>.
Ferreira et al., "Lewis acid deprotection of silyl-protected oligonucleotides and base-sensitive oligonucleotide analogues," Tetrahedron Lett. 45(33):6287-90 (2004).

Frankel et al., "Cellular Uptake of the Tat Protein from Human Immunodeficiency Virus," Cell. 55(6):1189-93 (1988).
Gillet et al., "Site-specific incorporation of N-(deoxyguanosin-8-yl)-2-acetylaminofluorene (dG-AAF) into oligonucleotides using modified 'ultra-mild' DNA synthesis," Nucleic Acids Res. 33(6):1961-9 (2005).
Green et al., "Autonomous Functional Domains of Chemically Synthesized Human Immunodeficiency Virus Tat Trans-activator Protein," Cell. 55(6):1179-88 (1988).
Guerlavais-Dagland et al., "Fluoride-labile protecting groups for the synthesis of base-sensitive methyl-SATE oligonucleotide prodrugs," Eur J Org Chem. 2327-35 (2003).
Gurevich et al., "Phosphorus-containing derivatives of indole and pyrrole (review)," Chemistry of Heterocyclic Compounds 36(12):1361-401 (2000).
Guzaev et al., "Synthesis of chimeric oligonucleotides containing internucleosidic phosphodiester and s-pivaloylthioethyl phosphotriester residues," Nucleosides Nucleotides Nucleic Acids. 20(4-7): 1015-8 (2001).
Guzaev et al., "Synthesis of chimerical oligonucleotides containing internucleosidic phosphodiester and s-pivaloyl mercaptoethyl phosphotriester linkages," Nucleosides & Nucleotides. 18(6-7):1391-2 (1999).
Hamilton et al., "A species of small antisense RNA in post-transcriptional gene silencing in plants," Science. 286(5441):950-2 (1999).
Hannon et al., "Unlocking the potential of the human genome with RNA interference," Nature. 431(7006):371-8 (2004).
Haussecker, "The RNAi Therapeutics Blog," https://rnaitherapeutics.blogspot.com/search?q=solstice, retrieved Mar. 23, 2020 (2013) (11 pages).
Hayakawa, "Toward an ideal synthesis of oligonucleotides: development of a novel phosphoramidite method with high capability," Bull Chem Soc Jpn. 74(9):1547-65 (2001).
Hecker et al., "Prodrugs of phosphates and phosphonates," J Med Chem. 51 (8):2328-45 (2008).
Huston et al., "Protein engineering of antibody binding sites: recovery of specific activity in an anti-digoxin single-chain Fv analogue produced in *Escherichia coli*," Proc Natl Acad Sci U.S.A. 85(16):5879-83 (1988).
International Search Report and Written Opinion for International Application No. PCT/US18/40592, dated Aug. 31, 2018 (28 pages).
Iyer et al., "3H-1,2-benzodithiole-3-one 1,1-dioxide as an improved sulfurizing reagent in the solid-phase synthesis of oligodeoxyribonucleoside phosphorothioates," J Am Chem Soc. 112:1253-4 (1990).
Joliot et al., "alpha-2,8-Polysialic acid is the neuronal surface receptor of antennapedia homeobox peptide," New Biol. 3(11):1121-34 (1991).
Joliot et al., "Antennapedia homeobox peptide regulates neural morphogenesis," Proc Natl Acad Sci U.S.A. 88(5):1864-8 (1991).
Joliot et al., "Transduction peptides: from technology to physiology," Nat Cell Biol. 6(3):189-96 (2004).
Josephson et al., "High-efficiency intracellular magnetic labeling with novel superparamagnetic-Tat peptide conjugates," Bioconjug Chem. 10(2):186-91 (1999).
Koppelhus et al., "Cell-dependent differential cellular uptake of PNA, peptides, and PNA-peptide conjugates," Antisense Nucleic Acid Drug Dev. 12(2):51-63 (2002) (19 pages).
Kosonen et al., "Hydrolysis and intramolecular transesterification of ribonucleoside 3'-phosphotriesters: the effect of alkyl groups on the general and specific acid-base-catalyzed reactions of 5'-O-pivaloyluridin-3'-yl dialkyl phosphates," J Chem Soc Perkin Trans 2. pp. 663-70 (1998).
Le Roux et al., "Neurotrophic activity of the Antennapedia homeodomain depends on its specific DNA-binding properties," Proc Natl Acad Sci U.S.A. 90(19):9120-4 (1993).
Letsinger et al., "Cationic oligonucleotides," J Am Chem Soc. 110(13):4470-1 (1988).
Leuschner et al., "Cleavage of the siRNA passenger strand during RISC assembly in human cells," EMBO Rep. 7(3):314-20 (2006).

(56) References Cited

OTHER PUBLICATIONS

Lewin et al., "Tat peptide-derivatized magnetic nanoparticles allow in vivo tracking and recovery of progenitor cells," Nat Biotechnol. 18(4):410-4 (2000).
Li et al., "Isolation and culture of adult mouse hepatocytes," Methods Mol Biol. 633:185-96 (2010).
Magzoub et al., "Modeling the endosomal escape of cell-penetrating peptides: transmembrane pH gradient driven translocation across phospholipid bilayers," Biochemistry 44(45):14890-7 (2005).
McGuigan et al., "Intracellular delivery of bioactive AZT nucleotides by aryl phosphate derivatives of AZT," J Med Chem. 36(8):1048-52 (1993).
Meade et al., "Efficient delivery of RNAi prodrugs containing reversible charge-neutralizing phosphotriester backbone modifications," Nat Biotechnol. 32(12):1256-61 (2014) (8 pages).
Meade, Bryan, Thesis: "Synthesis of Bioreversible, Phosphotriester-Modified siRNA Oligonucleotides," Doctor of Philosophy, Department of Cellular and Molecular Medicine, University of California San Diego, 2010.
Meister et al., "Mechanisms of gene silencing by double-stranded RNA," Nature 431 (7006):343-9 (2004).
Micklefield, "Backbone modification of nucleic acids: synthesis, structure and therapeutic applications," Curr Med Chem. 8(10):1157-79 (2001).
Nagahara et al., "Transduction of full-length TAT fusion proteins into mammalian cells: TAT-p27Kip1 induces cell migration," Nat Med. 4(12):1449-52 (1998).
Newton et al., "Angiogenin single-chain immunofusions: influence of peptide linkers and spacers between fusion protein domains," Biochemistry. 35(2):545-53 (1996).
Ng et al., "An anti-transferrin receptor-avidin fusion protein exhibits both strong proapoptotic activity and the ability to deliver various molecules into cancer cells," Proc Natl Acad Sci U.S.A. 99(16):10706-11 (2002).
Novina et al., "The RNAi revolution," Nature. 430(6996):161-4 (2004).
Paolella et al., "Electrostatic mechanism for DNA bending by bZIP Proteins," Biochemistry. 36(33):10033-8 (1997).
Parrish et al., "Functional anatomy of a dsRNA trigger: differential requirement for the two trigger strands in RNA interference," Mol Cell. 6(5):1077-87 (2000).
Polyakov et al., "Novel Tat-peptide chelates for direct transduction of technetium-99m and rhenium into human cells for imaging and radiotherapy," Bioconjug Chem. 11 (6):762-71 (2000).
Rattan et al., "Protein synthesis, posttranslational modifications, and aging," Ann N Y Acad Sci. 663:48-62(1992).
Schlienger et al., "S-Acyl-2-thioethyl aryl phosphotriester derivatives as mononucleotide prodrugs," J Med Chem. 43(23):4570-4 (2000).
Schmidt et al., "RNA cleavage by hybridase. IV. Oligonucleotide probes with 2'-deoxy-2'-fluoronucleosides and arabinofuranosylcytosine," Bioorganicheskaya Khimiya. 17(6):823-30 (1991).
Schwarze et al., "In vivo protein transduction: delivery of a biologically active protein into the mouse," Science. 285(5433):1569-72 (1999).
Seifter et al., "Analysis for protein modifications and nonprotein cofactors," Methods Enzymol. 182:626-46 (1990).
Shafiee et al., "New bis(SATE) prodrug of AZT 5'-monophosphate: In vitro anti-HIV activity, stability, and potential oral absorption," J Pharm Sci. 90(4):448-63 (2001).
Snyder et al., "Recent advances in the use of protein transduction domains for the delivery of peptides, proteins and nucleic acids in vivo," Expert Opin Drug Deliv. 2(1):43-51 (2005).
Sontheimer, "Assembly and function of RNA silencing complexes," Nat Rev Mol Cell Biol. 6(2):127-38 (2005).
Spinelli et al., "Use of allylic protecting groups for the synthesis of base-sensitive prooligonucleotides," Eur J Org Chem. 49-56 (2002).
Tanabe et al., "Chemical ligation of oligodeoxynucleotides by X-irradiation and its application to regulation of G-quadruplex formation," Bioorg Med Chem Lett. 23(7):2098-2100 (2013).
Tosquellas et al., "The pro-oligonucleotide approach: solid phase synthesis and preliminary evaluation of model pro-dodecathymidylates," Nucleic Acids Res. 26(9):2069-74 (1998).
Turner et al., "RNA targeting with peptide conjugates of oligonucleotides, siRNA and PNA," Blood Cells Mol Dis. 38:1-7 (2007).
Villard et al., "Phenyl phosphotriester derivatives of AZT: Variations upon the SATE moiety," Bioorg Med Chem. 16(15):7321-9 (2008).
Wagner et al., "Pronucleotides: Toward the in vivo delivery of antiviral and anticancer nucleotides," Med Res Rev. 20(6):417-51 (2000).
Whitlow et al., "An improved linker for single-chain Fv with reduced aggregation and enhanced proteolytic stability," Protein Eng. 6(8):989-95 (1993).
Wunderbaldinger et al., "Tat peptide directs enhanced clearance and hepatic permeability of magnetic nanoparticles," Bioconjug Chem. 13(2):264-8 (2002).
Xie et al., "Harnessing in vivo siRNA delivery for drug discovery and therapeutic development," Drug Discov Today. 11(1-2):67-73 (2006).
Zuckermann et al., "Efficient methods for attachment of thiol specific probes to the 3'-ends of synthetic oligodeoxyribonucleotides," Nucleic Acids Res. 15(13):5305-21 (1987).
Iwamoto et al. (PSJ Congress: The Pharmaceutical Society of Japan, (Mar. 25-28, 2015) (Year: 2015).
Li et al., "Chiral Amino Alcohol Derived Bis-phosphoramidite Pincer Palladium Complexes and Their Applications in Asymmetric Allylation of Aldimines," Organometallics. 29:1379-1387 (2010).
Aaronson et al. Rapid HATU-mediated solution phase siRNA conjugation. Bioconjugate Chem. 22:1723-1728 (2011).
Caruthers. Chapter 1: Synthesis of Oligonucleotides and Oligonucleotide Analogues. Oligonucleotides: Antisense Inhibitors of Gene Expression. J. S. Cohen, ed. CRC Press, Inc. Boca Raton, Fla., (pp. 7-24) (1989).
Dodd, et al. Normal T-cell response and in vivo magnetic resonance imaging of T cells loaded with HIV transactivator-peptide-derived superparamagnetic nanoparticles. J Immunol Methods. Oct. 1, 2001;256(1-2):89-105.
El-Sagheer et al. Synthesis of alkyne- and azide-modified oligonucleotides and their cyclization by the CuAAC (click) reaction. Curr Protoc Nucleic Acid Chem Chapter 4:Unit 4.33 (2008).
Englisch et al. Chemically Modified Oligonucleotides as Probes and Inhibitors. Angew. Chem. Int. Ed. Eng. 30:613-629 (1991).
Lamoyi et al. Preparation of F(ab')2 fragments from mouse IgG of various subclasses. J. Immunol Methods 56:235-243 (1983).
Lennartz et al. Isolation and characterization of a mannose-specific endocytosis receptor from human placenta. J. Biol. Chem. 262:9942-9944 (1987).
Oka et al. Stereocontrolled synthesis of oligonucleotide analogs containing chiral internucleotidic phosphorus atoms. Chem. Soc. Rev. 40:5829-5843 (2011).
Oka et al. Stereocontrolled synthesis of oligoribonucleoside phosphorothioates by an oxazaphospholidine approach. Org. Lett. 11:967-970 (2009).
PARHAM. On the fragmentation of monoclonal IgG 1, IgG2a, and IgG2b from BALB/c mice. J. Immunol 131:2895-902 (1983).
PCT/US2017/047447 International Search Report and Written Opinion dated Jan. 4, 2018.
Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).
Taylor et al. Primary structure of the mannose receptor contains multiple motifs resembling carbohydrate-recognition domains. J. Biol. Chem. 265:12156-62 (1990).
The Concise Encyclopedia of Polymer Science and Engineering, Kroschwitz, J.I., Ed., John Wiley & Sons pp. 858-859 (1990).
U.S. Appl. No. 16/326,542 Office Action dated Feb. 9, 2022.

(56) References Cited

OTHER PUBLICATIONS

Wu et al. 2'-OMe-phosphorodithioate-modified siRNAs show increased loading into the RISC complex and enhanced anti-tumour activity. Nat. Commun. 5:3459 (2013).
Yang et al. Gene silencing activity of siRNA molecules containing phosphorodithioate substitutions. ACS Chem. Biol. 7:1214-1220 (2012).

\* cited by examiner

CHIRAL PHOSPHORAMIDITE AUXILIARIES AND METHODS OF THEIR USE

CROSS-REFERENCE TO RELATED APPLICATIONS

This application is a U.S. National Entry Application of International Application No. PCT/US2018/040592, filed internationally on Jul. 2, 2018, which claims the benefit of U.S. Provisional Application Ser. No. 62/527,078, filed on Jun. 30, 2017, all of which are incorporated by reference in their entireties.

FIELD OF THE INVENTION

The invention relates to chiral auxiliaries and reagents useful for diastereoselective syntheses of P-stereogenic phosphites, phosphates, and phosphorothioates. The invention also relates to the preparation of oligonucleotides and methods of making chiral reagents.

BACKGROUND

Oligonucleotides including phosphorothioate phosphodiesters have two possible oligonucleotide diastereomers for each P-stereogenic phosphorothioate. Many oligonucleotide therapeutics include multiple P-stereogenic phosphorothioates and thus have $2^n$ possible diastereomers, where n is the number of P-stereogenic phosphorothioates. For example, an oligonucleotide containing six phosphorothioate phosphodiesters has 64 possible different diastereomers, which collectively can form over $10^{19}$ different diastereomeric mixtures. Separation of oligonucleotide diastereomers is impractical, in view of the material losses in the form of other diastereomers and the complexity of method development for oligonucleotide diastereomer separation. Accordingly, synthesis of oligonucleotides including P-stereogenic phosphorothioates requires development of reagents and methods for stereoselective introduction of P-stereogenic phosphorothioates. The currently available chiral reagents typically require lengthy synthetic routes. New reagents and methods for the synthesis of oligonucleotides including stereochemically enriched P-stereogenic phosphorothioates are needed.

SUMMARY OF THE INVENTION

In general, the present invention provides P-stereogenic groups, compounds containing them, and methods for diastereoselective synthesis of, e.g., oligonucleotides including stereochemically enriched internucleoside phosphorothioates.

In one aspect, the invention provides a P-stereogenic group of formula (IA), (IB), (IC), or (ID):

(IA)
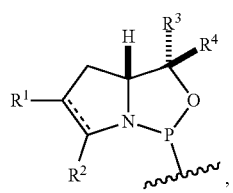

(IB)
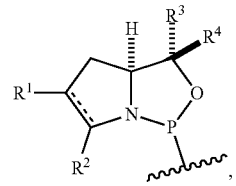

(IC)
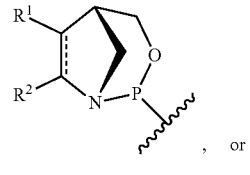

or (ID)
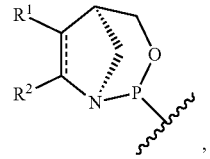

where
═ is a single carbon-carbon bond or a double carbon-carbon bond;
each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and
each of $R^3$ and $R^4$ is independently H, optionally substituted $C_{1-6}$ alkyl, or optionally substituted $C_{6-10}$ aryl.

In some embodiments, the P-stereogenic group is of formula (IA) or (IB). In certain embodiments, $R^1$ and $R^2$, together with the atoms to which each is attached, combine to form an optionally substituted 5- to 8-membered ring (e.g., an optionally substituted 5- to 8-membered carbocyclic ring (e.g., optionally substituted 5- to 8-membered ring is an optionally substituted 6-membered carbocyclic ring)).

In particular embodiments, the P-stereogenic group is of the following structure:

(IIA)
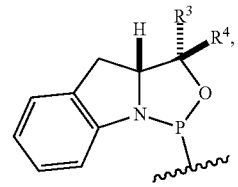

(IIB)
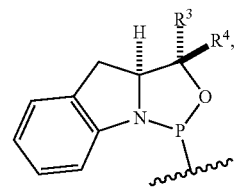

(IIC)
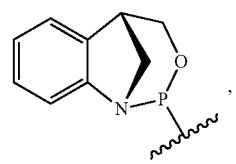

-continued

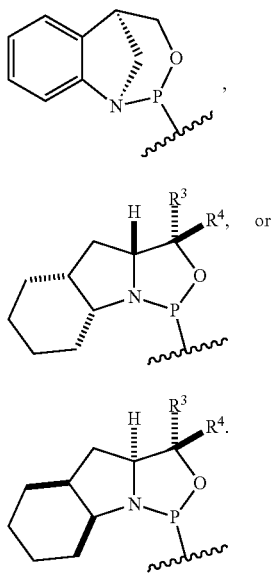

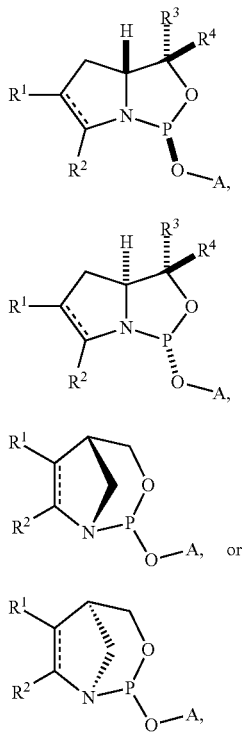

In further embodiments, R³ is H. In yet further embodiments, R⁴ is H. In still further embodiments, R³ and R⁴ are each H.

In certain embodiments, the P-stereogenic group is of formula (IIA), (IIB), (IIA'), or (IIB').

In another aspect, the invention provides a compound of formula (IIIA), (IIIB), (IIIC), or (IIID):

(IIIA)

(IIIB)

(IIIC)

(IIID)

where
═ is a single carbon-carbon bond or a double carbon-carbon bond;
A is an optionally substituted $C_{1-12}$ alkyl, optionally substituted $C_{3-10}$ cycloalkyl, optionally substituted $C_{3-10}$ cycloalkyl-$C_{1-6}$-alkyl, optionally substituted $C_{1-9}$ heterocyclyl, optionally substituted $C_{1-9}$ heterocyclyl-$C_{1-6}$-alkyl, sugar analogue, nucleoside, nucleotide, or oligonucleotide;
each of R¹ and R² is independently an optionally substituted $C_{1-6}$ alkyl or optionally substituted $C_{6-10}$ aryl, or R¹ and R², together with the atoms to which each is attached, combine to form an optionally substituted 5- to 8-membered ring; and
each of R³ and R⁴ is independently H, optionally substituted $C_{1-6}$ alkyl, or optionally substituted $C_{6-10}$ aryl.

In some embodiments, the compound is of formula (IIIA) or (IIIB).

In certain embodiments, R¹ and R², together with the atoms to which each is attached, combine to form an optionally substituted 5- to 8-membered ring (e.g., optionally substituted 5- to 8-membered carbocyclic ring (e.g., optionally substituted 6-membered carbocyclic ring)).

In particular embodiments, the compound is of the following structure:

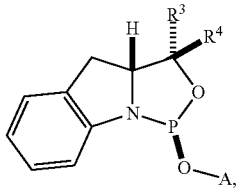
(IVA)

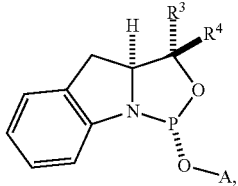
(IVB)

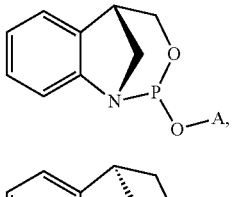
(IVC)

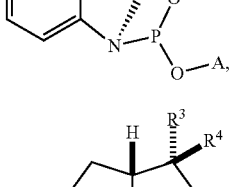
(IVD)

(IVA')

(IVB')

In further embodiments, $R^3$ is H. In yet further embodiments, $R^4$ is H. In still further embodiments, $R^3$ and $R^4$ are each H.

In other embodiments, the compound is of formula (IVA), (IVB), (IVA'), or (IVB').

In yet another aspect, the invention provides a nucleoside phosphoramidite including a sugar bonded to a nucleobase and to a phosphoramidite of the following structure:

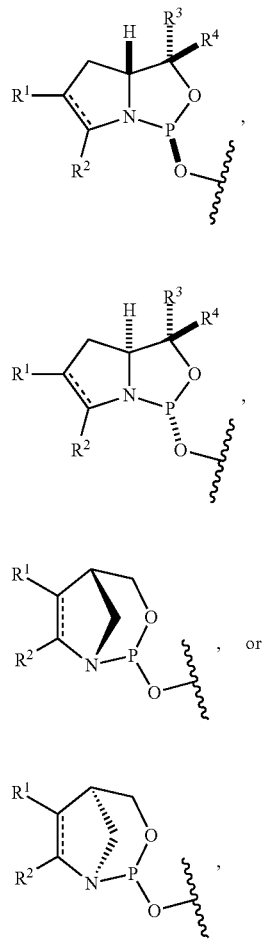

where

=== is a single carbon-carbon bond or a double carbon-carbon bond;

each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and each of $R^3$ and $R^4$ is independently H, optionally substituted $C_{1-6}$ alkyl, or optionally substituted $C_{6-10}$ aryl.

In some embodiments, the nucleoside phosphoramidite includes a phosphoramidite of formula (VA) or (VB).

In certain embodiments, the nucleoside phosphoramidite is of the following structure:

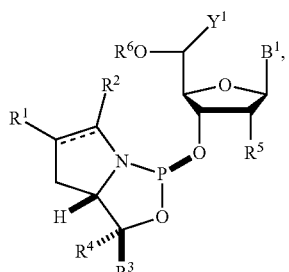

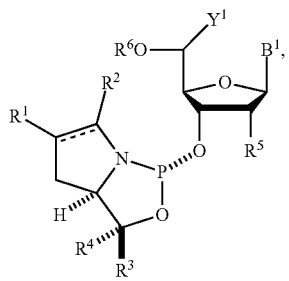

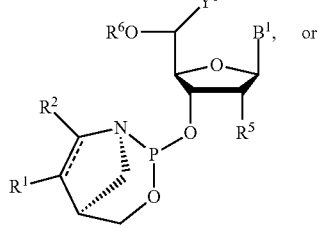

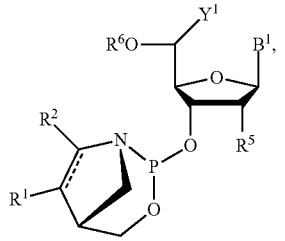

where $B^1$ is a nucleobase;

$Y^1$ is H or $C_{1-6}$ alkyl;

$R^5$ is H, O-protected hydroxyl, optionally substituted $C_{1-6}$ alkoxy, or halogen; and $R^6$ is a hydroxyl protecting group.

In particular embodiments, the nucleoside phosphoramidite is of formula (VIA) or (VIB).

In further embodiments, $R^5$ is hydrogen, halogen, or optionally substituted $C_{1-6}$ alkoxy. In yet further embodiments, $R^5$ is hydrogen, fluoro, or methoxy. In still further embodiments, $R^6$ is dimethoxytrityl.

In some embodiments, $R^1$ and $R^2$, together with the atoms to which each is attached, combine to form an optionally substituted 5- to 8-membered ring (e.g., optionally substituted 5- to 8-membered carbocyclic ring (e.g., optionally substituted 6-membered carbocyclic ring)).

In certain embodiments, the phosphoramidite is of the following structure:

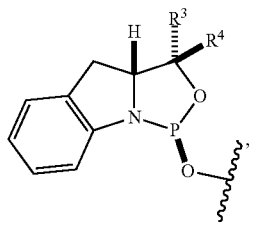
(VIIA)

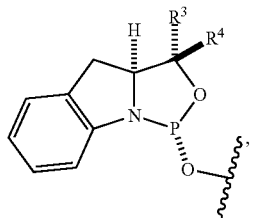
(VIIB)

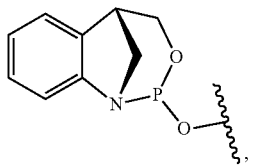
(VIIC)

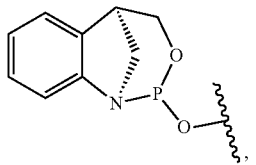
(VIID)

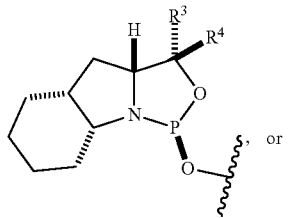
(VIIA′)

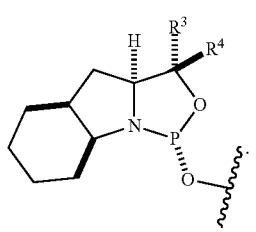
(VIIB′)

In further embodiments, $R^3$ is H. In yet further embodiments, $R^4$ is H. In still further embodiments, $R^3$ and $R^4$ are each H.

In still another aspect, the invention provides a compound of formula:

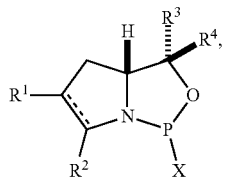
(VIIIA)

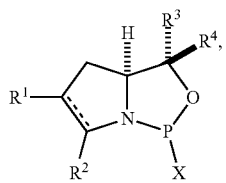
(VIIIB)

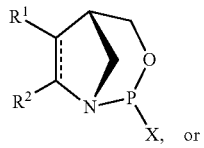
(VIIIC)

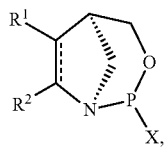
(VIIID)

where
≡ is a single carbon-carbon bond or a double carbon-carbon bond;
X is a halogen or pseudohalogen;
each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and
each of $R^3$ and $R^4$ is independently H, optionally substituted $C_{1-6}$ alkyl, or optionally substituted $C_{6-10}$ aryl.

In certain embodiments, the compound is of formula (VIIIA) or (VIIIB).

In some embodiments, $R^1$ and $R^2$, together with the atoms to which each is attached, combine to form an optionally substituted 5- to 8-membered ring (e.g., optionally substituted 5- to 8-member carbocyclic ring (e.g., optionally substituted 6-member carbocyclic ring)).

In particular embodiments, the compound is of the following structure:

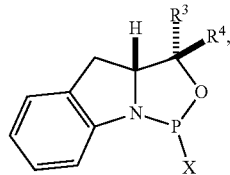
(IXA)

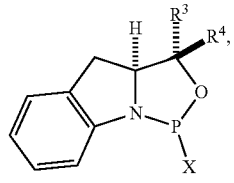
(IXB)

-continued

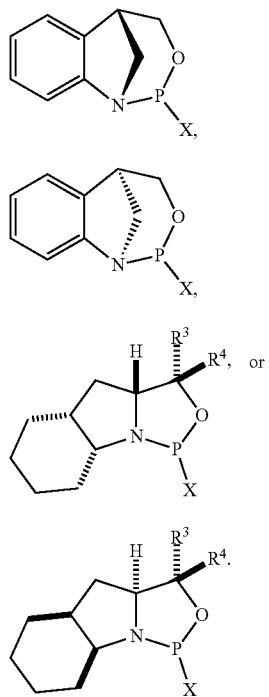

(IXC)

(IXD)

(IXA')

(IXB')

In some embodiments, the compound is of formula (IXA), (IXB), (IXA'), or (IXB').

In further embodiments, $R^3$ is H. In yet further embodiments, $R^4$ is H. In still further embodiments, $R^3$ and $R^4$ are each H.

In a further aspect, the invention provides a method of preparing a composition containing an oligonucleotide including a stereochemically enriched internucleoside phosphorothioate by (i) reacting the nucleoside phosphoramidite disclosed herein with a coupling activator and a nucleoside including a 5'-hydroxyl or an oligonucleotide including a 5'-hydroxyl, (ii) reacting with an electrophilic source of acyl, and (iii) reacting with a sulfurizing agent to produce the oligonucleotide containing a stereochemically enriched internucleoside phosphorothioate triester.

In some embodiments, the method further includes converting the phosphorothioate triester into a phosphorothioate diester by reacting the phosphorothioate triester with an aqueous base.

In particular embodiments, the coupling activator is 5-(benzylthio)-1H-tetrazole (BTT), N-(phenyl)imidazolium trifluoromethanesulfonate (PhIMT), or N-(cyanomethyl)pyrrolidinium trifluoromethanesulfonate (CMPT). In certain embodiments, the coupling activator is CMPT.

In further embodiments, the nucleoside is a 2'-deoxyribonucleoside. In yet further embodiments, the electrophilic source of acyl is an acid anhydride (e.g., acetic anhydride or trifluoroacetic anhydride). In still further embodiments, the sulfurizing agent is 3-((N,N-dimethylaminomethylidene)amino)-3H-1,2,4-dithiazole-5-thione (DDTT).

In yet further aspect, the invention provides a method of preparing the nucleoside phosphoramidite including a sugar bonded to a nucleobase and phosphoramidite of the following structure:

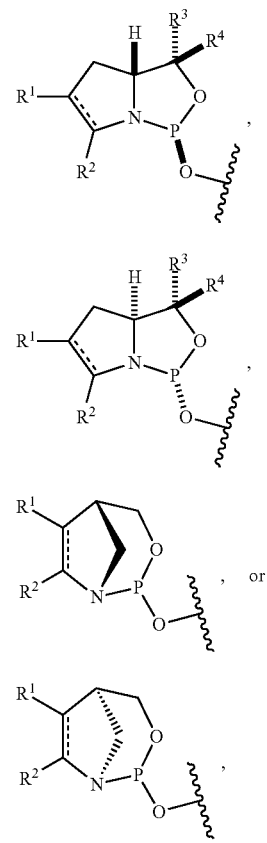

(VA)

(VB)

(VC)

(VD)

where

═ is a single carbon-carbon bond or a double carbon-carbon bond;

each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and each of $R^3$ and $R^4$ is independently H, optionally substituted $C_{1-6}$ alkyl, or optionally substituted $C_{6-10}$ aryl;

by reacting a sugar bonded to a nucleobase with a compound of formula (VIIIA), (VIIIB), (VIIIC), or (VIIID):

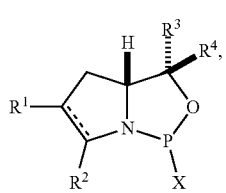

(VIIIA)

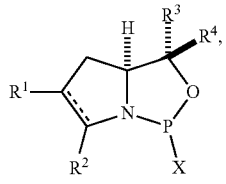

(VIIIB)

-continued

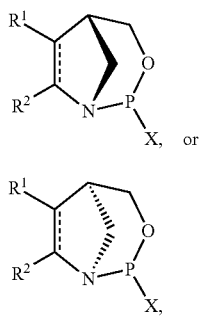
(VIIIC)

(VIIID)

where
X is a halogen or pseudohalogen.

In particular embodiments, the nucleoside phosphoramidite is of formula (VA) or (VB), and a sugar bonded to a nucleobase is reacted with a compound of formula (VIIIA) or (VIIIB).

In a further aspect, the invention provides an oligonucleotide (e.g., an oligonucleotide having a total of 2-100 nucleosides (e.g., 2 to 50 or 2 to 35) including one or more (e.g., 1 to 6, 1 to 5, 1 to 4, 1 to 3, 1 to 2, or 1) internucleoside groups independently selected from the group consisting of linkers of formula (XIA) and (XIB):

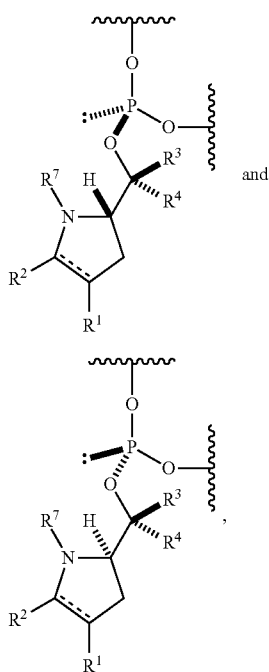
(XIA)

and (XIB)

where
═ is a single carbon-carbon bond or a double carbon-carbon bond;
each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring;
each of $R^3$ and $R^4$ is independently H, optionally substituted $C_{1-6}$ alkyl, or optionally substituted $C_{6-10}$ aryl; and
$R^7$ is acyl (e.g., alkanoyl).

In certain embodiments, $R^1$ and $R^2$, together with the atoms to which each is attached, combine to form an optionally substituted 5- to 8-membered ring (e.g., optionally substituted 5- to 8-membered carbocyclic ring (e.g., optionally substituted 6-membered carbocyclic ring)).

In some embodiments, the one or more (e.g., 1 to 6, 1 to 5, 1 to 4, 1 to 3, 1 to 2, or 1) internucleoside groups are selected from the group of linkers of formula (XIIIA), (XIIIB), (XIIIA'), and (XIIIB'):

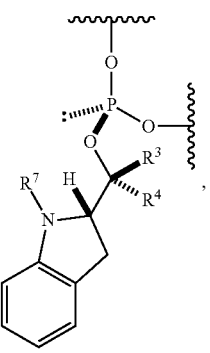
(XIIIA)

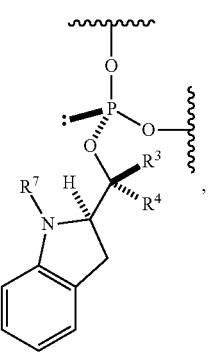
(XIIIB)

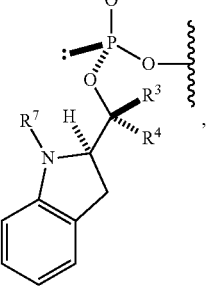
(XIIIA')

and

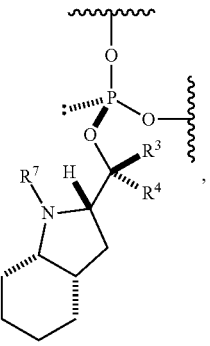

(XIIIB')

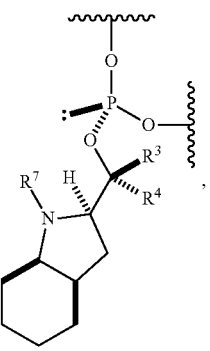

where
- === is a single carbon-carbon bond or a double carbon-carbon bond;
- each of $R^3$ and $R^4$ is independently H, optionally substituted $C_{1-6}$ alkyl, or optionally substituted $C_{6-10}$ aryl; and
- $R^7$ is acyl (e.g., alkanoyl).

In further embodiments, $R^3$ is H. In yet further embodiments, $R^4$ is H. In still further embodiments, $R^3$ and $R^4$ are each H.

In a yet further aspect, the invention provides an oligonucleotide (e.g., an oligonucleotide having a total of 2-100 nucleosides (e.g., 2 to 50 or 2 to 35) including one or more (e.g., 1 to 6, 1 to 5, 1 to 4, 1 to 3, 1 to 2, or 1) internucleoside groups independently selected from the group consisting of linkers of formula (XIIA) and (XIIB):

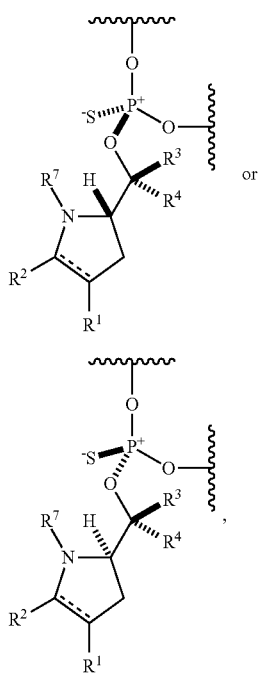

where
- === is a single carbon-carbon bond or a double carbon-carbon bond;
- each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring;
- each of $R^3$ and $R^4$ is independently H, optionally substituted $C_{1-6}$ alkyl, or optionally substituted $C_{6-10}$ aryl; and
- $R^7$ is acyl (e.g., alkanoyl).

In certain embodiments, $R^1$ and $R^2$, together with the atoms to which each is attached, combine to form an optionally substituted 5- to 8-membered ring (e.g., optionally substituted 5- to 8-membered carbocyclic ring (e.g., optionally substituted 6-membered carbocyclic ring)).

In some embodiments, the one or more (e.g., 1 to 6, 1 to 5, 1 to 4, 1 to 3, 1 to 2, or 1) internucleoside groups are selected from the group of linkers of formula (XIVA), (XIVB), (XIVA'), and (XIVB'):

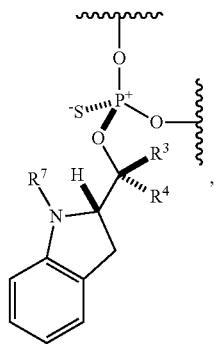

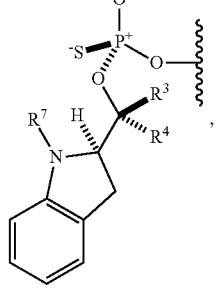

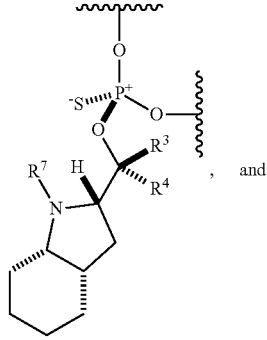

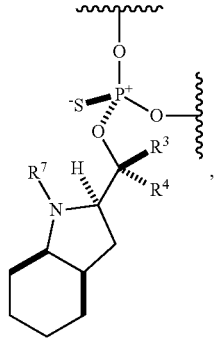

where
- === is a single carbon-carbon bond or a double carbon-carbon bond;
- each of $R^3$ and $R^4$ is independently H, optionally substituted $C_{1-6}$ alkyl, or optionally substituted $C_{6-10}$ aryl; and
- $R^7$ is acyl (e.g., alkanoyl).

In further embodiments, $R^3$ is H. In yet further embodiments, $R^4$ is H. In still further embodiments, $R^3$ and $R^4$ are each H.

Definitions

The term "abasic spacer," as used herein, refers to internucleoside, abasic spacers known in the art, e.g., those described in WO 2018/035380. For example, an abasic spacer may be a group of formula (X'):

where
- each of $R^{A1}$ and $R^{A2}$ is independently H, $-OR^{A4}$, or $-N(R^{A4})(R^{A5})$; where $R^{A4}$ is optionally substituted $C_{1-16}$ alkyl, optionally substituted $C_{2-16}$ heteroalkyl, or a protecting group, and $R^{A5}$ is H optionally substituted $C_{1-16}$ alkyl, optionally substituted $C_{2-16}$ heteroalkyl, or a protecting group; and
- each of m1, m2, m3, and m4 is independently an integer from 0 to 11, provided that the quaternary carbon in the structure above is bonded to 0 or 1 atoms other than carbon and hydrogen, and provided that the sum of m1, m2, m3 and m4 is 11 or less.

The term "about," as used herein, represents a value that is ±10% of the recited value.

The term "acyl," as used herein, represents a group of formula $-C(O)-R^1$, where $R^1$ is H, alkyl, aryl, or heteroaryl. Acyl may be optionally substituted as defined for the group present as $R^1$ in acyl. Acyl, in which $R^1$ is alkyl (e.g., optionally substituted alkyl), may be referred to as an alkanoyl. Acyl, in which $R^1$ is aryl (e.g., optionally substituted aryl), may be referred to as an aryloyl. Acyl, in which $R^1$ is heteroaryl (e.g., optionally substituted heteroaryl), may be referred to as an heteroaryloyl.

The term "acyloxy," as used herein, represents a group of formula $-OR$, where R is acyl. Acyloxy may be optionally substituted as defined for acyl. Acyloxy, in which R is alkanoyl (e.g., optionally substituted alkanoyl), may be referred to as an alkanoyloxy. Acyl, in which R is aryloyl (e.g., optionally substituted aryloyl), may be referred to as an aryloyloxy. Acyl, in which R is heteroaryloyl (e.g., optionally substituted heteroaryloyl), may be referred to as an heteroaryloyloxy.

The term "alkanoylamino," as used herein, represents a group of formula $-NHR$, where R is alkanoyl.

The term "alkenyl," as used herein, represents acyclic monovalent straight or branched chain hydrocarbon groups of containing one, two, or three carbon-carbon double bonds. An unsubstituted alkenyl includes 2 to 16 carbon atoms. Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted with 1, 2, 3, or 4 substituent groups selected, independently, from the group consisting of aryl, cycloalkyl, heterocyclyl (e.g., heteroaryl), as defined herein, and the substituent groups described for alkyl.

The term "alkenylene," as used herein, refers to a straight or branched chain alkenyl group with one hydrogen removed, thereby rendering this group divalent. The valency of alkenylene defined herein does not include the optional substituents. Non-limiting examples of the alkenylene groups include ethen-1,1-diyl; ethen-1,2-diyl; prop-1-en-1,1-diyl, prop-2-en-1,1-diyl; prop-1-en-1,2-diyl, prop-1-en-1,3-diyl; prop-2-en-1,1-diyl; prop-2-en-1,2-diyl; but-1-en-1,1-diyl; but-1-en-1,2-diyl; but-1-en-1,3-diyl; but-1-en-1,4-diyl; but-2-en-1,1-diyl; but-2-en-1,2-diyl; but-2-en-1,3-diyl; but-2-en-1,4-diyl; but-2-en-2,3-diyl; but-3-en-1,1-diyl; but-3-en-1,2-diyl; but-3-en-1,3-diyl; but-3-en-2,3-diyl; buta-1,2-dien-1,1-diyl; buta-1,2-dien-1,3-diyl; buta-1,2-dien-1,4-diyl; buta-1,3-dien-1,1-diyl; buta-1,3-dien-1,2-diyl; buta-1,3-dien-1,3-diyl; buta-1,3-dien-1,4-diyl; buta-1,3-dien-2,3-diyl; buta-2,3-dien-1,1-diyl; and buta-2,3-dien-1,2-diyl. The alkenylene group may be unsubstituted or substituted (e.g., optionally substituted alkenylene) as described for alkenyl groups.

The term "alkenoxy," as used herein, represents a chemical substituent of formula $-OR$, where R is an alkenyl group, unless otherwise specified. An alkenyloxy group may be substituted or unsubstituted (e.g., optionally substituted alkenyloxy) as described herein for alkyl groups.

The term "alkoxy," as used herein, represents a chemical substituent of formula $-OR$, where R is a $C_{1-6}$ alkyl group, unless otherwise specified. In some embodiments, the alkyl group can be optionally substituted in the manner described for alkyl groups.

The term "alkoxycarbonyl," as used herein, represents a chemical substituent of formula $-COOR$, where R is alkyl. An alkoxycarbonyl group may be substituted or unsubstituted (e.g., optionally substituted alkoxycarbonyl) as described herein for alkyl groups.

The term "alkyl," as used herein, refers to an acyclic straight or branched chain saturated hydrocarbon group having from 1 to 16 carbons (when unsubstituted), unless otherwise specified. Alkyl groups are exemplified by methyl; ethyl; n- and iso-propyl; n-, sec-, iso- and tert-butyl; neopentyl, and the like, and may be optionally substituted with one, two, three, or, in the case of alkyl groups of two carbons or more, four substituents independently selected from the group consisting of: (1) alkoxy; (2) alkylsulfinyl; (3) amino; (4) arylalkoxy; (5) (arylalkyl)aza; (6) azido; (7) halo; (8) (heterocyclyl)oxy; (9) (heterocyclyl)aza; (10) hydroxy; (11) nitro; (12) oxo; (13) aryloxy; (14) sulfide; (15) thioalkoxy; (16) thiol; (17) aryl; (18) $-CO_2R^A$, where $R^A$ is selected from the group consisting of (a) alkyl, (b) aryl, (c) hydrogen, and (d) arylalkyl; (19) $-C(O)NR^BR^C$, where each of $R^B$ and $R^C$ is, independently, selected from the group consisting of (a) hydrogen, (b) alkyl, (c) aryl, and (d) arylalkyl; (20) $-SO_2R^D$, where $R^D$ is selected from the group consisting of (a) alkyl, (b) aryl, and (c) arylalkyl; (21) $-SO_2NR^ER^F$, where each of $R^E$ and $R^F$ is, independently, selected from the group consisting of (a) hydrogen, (b) alkyl, (c) aryl and (d) arylalkyl; (22) silyl; (23) cyano; and (24) $-S(O)R^H$ where $R^H$ is selected from the group consisting of (a) hydrogen, (b) alkyl, (c) aryl, and (d) arylalkyl. In some embodiments, each of these groups can be further substituted with unsubstituted substituents as described herein for each respective group.

The term "alkylamino," as used herein, refers to a group $-N(R^{N1})_2$, in which each $R^{N1}$ is independently H or alkyl, provided that at least one $R^{N1}$ is alkyl. Alkylamino may be optionally substituted; each alkyl in optionally substituted alkylamino is independently and optionally substituted as described for alkyl.

The term "alkylaminocarbonyl," as used herein, represents a chemical substituent of formula $R-(CO)-$, where R is alkylamino.

The term "alkylaminoalkylaminocarbonyl," as used herein, represents a chemical substituent of formula $R^1$—$R^2$—NH—(CO)—, where $R^1$ is alkylamino, and $R^2$ is alkylene.

The term "alkylene," as used herein, refers to a saturated divalent hydrocarbon group derived from a straight or branched chain saturated hydrocarbon by the removal of two hydrogen atoms. The valency of alkylene defined herein does not include the optional substituents. Non-limiting examples of the alkylene group include methylene, ethane-1,2-diyl, ethane-1,1-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, and butane-2,2-diyl, butane-2,3-diyl. The term "$C_{x-y}$ alkylene" represents alkylene groups having between x and y carbons. Exemplary values for x are 1, 2, 3, 4, 5, and 6, and exemplary values for y are 2, 3, 4, 5, 6, 7, 8, 9, 10, 11, and 12. In some embodiments, the alkylene can be optionally substituted with 1, 2, 3, or 4 substituent groups as defined herein for an alkyl group. Similarly, the suffix "ene" designates a divalent radical of the corresponding monovalent radical as defined herein. For example, alkenylene, alkynylene, arylene, aryl alkylene, cycloalkylene, cycloalkyl alkylene, cycloalkenylene, heteroarylene, heteroaryl alkylene, heterocyclylene, and heterocyclyl alkylene are divalent forms of alkenyl, alkynyl, aryl, aryl alkyl, cycloalkyl, cycloalkyl alkyl cycloalkenyl, heteroaryl, heteroaryl alkyl, heterocyclyl, and heterocyclyl alkyl. For aryl alkylene, cycloalkyl alkylene, heteroaryl alkylene, and heterocyclyl alkylene, the two valences in the group may be located in the acyclic portion only or one in the cyclic portion and one in the acyclic portion. For example, the alkylene group of an aryl-$C_1$-alkylene or a heterocyclyl-$C_1$-alkylene can be further substituted with an oxo group to afford the respective aryloyl and (heterocyclyl)oyl substituent group.

The term "alkyleneoxy," as used herein, refers to a divalent group —R—O—, in which R is alkylene. Alkylene in alkyleneoxy may be unsubstituted or substituted (e.g., optionally substituted alkyleneoxy) as described for alkyl.

The term "alkylsulfonyl," as used herein, refers to a group —$SO_2$—R, where R is alkyl.

The term "alkylsulfonyloxy," as used herein, refers to a group —OR, where R is alkylsulfonyl.

The term "alkynyl," as used herein, represents monovalent straight or branched chain hydrocarbon groups of from two to sixteen carbon atoms containing at least one carbon-carbon triple bond and is exemplified by ethynyl, 1-propynyl, and the like. Alkynyl groups may be optionally substituted with 1, 2, 3, or 4 substituent groups that are selected, independently, from aryl, alkenyl, cycloalkyl, and heterocyclyl (e.g., heteroaryl), as described herein, and the substituent groups described for alkyl.

The term "alkynylene," as used herein, refers to a straight-chain or branched-chain divalent substituent including one or two carbon-carbon triple bonds and containing only C and H when unsubstituted. An unsubstituted alkynylene contains from two to sixteen carbon atoms, unless otherwise specified. The valency of alkynylene defined herein does not include the optional substituents. Non-limiting examples of the alkenylene groups include ethyn-1,2-diyl; prop-1-yn-1,3-diyl; prop-2-yn-1,1-diyl; but-1-yn-1,3-diyl; but-1-yn-1,4-diyl; but-2-yn-1,1-diyl; but-2-yn-1,4-diyl; but-3-yn-1,1-diyl; but-3-yn-1,2-diyl; but-3-yn-2,2-diyl; and buta-1,3-diyn-1,4-diyl. The alkynylene group may be unsubstituted or substituted (e.g., optionally substituted alkynylene) as described for alkynyl groups.

The term "amino," as used herein, represents —N($R^{N1}$)$_2$, where, if amino is unsubstituted, both $R^{N1}$ are H; or, if amino is substituted, each $R^{N1}$ is independently H, —OH, —$NO_2$, —N($R^{N2}$)$_2$, —N(R)$SO_2OR^{N2}$, —$SO_2R^{N2}$, —$SOR^{N2}$, —$COOR^{N2}$, an N-protecting group, alkyl, alkenyl, alkynyl, alkoxy, aryl, arylalkyl, aryloxy, cycloalkyl, cycloalkenyl, heteroalkyl, or heterocyclyl, provided that at least one $R^{N1}$ is not H, and where each $R^{N2}$ is independently H, alkyl, or aryl. Each of the substituents may itself be unsubstituted or substituted with unsubstituted substituent(s) defined herein for each respective group. In some embodiments, amino is unsubstituted amino (i.e., —$NH_2$) or substituted amino (e.g., —$NHR^{N1}$), where $R^{N1}$ is independently —OH, —$SO_2OR^{N2}$, —$SO_2R^{N2}$, —$SOR^{N2}$, —$COOR^{N2}$, optionally substituted alkyl, or optionally substituted aryl, and each $R^{N2}$ can be optionally substituted alkyl or optionally substituted aryl. In some embodiments, substituted amino may be alkylamino, in which the alkyl group is optionally substituted as described herein for alkyl. In further embodiments, substituted amino may be dialkylamino, in which the alkyl groups are optionally substituted as described herein for alkyl. In certain embodiments, an amino group is —$NHR^{N1}$, in which $R^{N1}$ is optionally substituted alkyl. Non-limiting examples of —$NHR^{N1}$, in which $R^{N1}$ is optionally substituted alkyl, include: optionally substituted alkylamino, a proteinogenic amino acid, a non-proteinogenic amino acid, a $C_{1-6}$ alkyl ester of a proteinogenic amino acid, and a $C_{1-6}$ alkyl ester of a non-proteinogenic amino acid.

The term "aminoalkyl," as used herein, represents a chemical substituent of formula —R'—R", where R' is alkylene, and R" is amino. Aminoalkyl may be optionally substituted as defined for each of the two portions.

The term "aminoalkylaminocarbonyl," as used herein, represents a chemical substituent of formula $R^1$—$R^2$—NH—(CO)—, where $R^1$ is amino, and $R^2$ is alkylene.

The term "aryl," as used herein, represents a mono-, bicyclic, or multicyclic carbocyclic ring system having one, two, or three (e.g., one or two) aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) acyl; (2) alkyl; (3) alkenyl; (4) alkynyl; (5) alkoxy; (6) alkylsulfinyl; (7) aryl; (8) amino; (9) arylalkyl; (10) azido; (11) cycloalkyl; (12) cycloalkylalkyl; (13) cycloalkenyl; (14) cycloalkenylalkyl; (15) halo; (16) heterocyclyl (e.g., heteroaryl); (17) (heterocyclyl)oxy; (18) (heterocyclyl)aza; (19) hydroxy; (20) nitro; (21) thioalkoxy; (22) —$(CH_2)_qCO_2R^A$, where q is an integer from zero to four, and $R^A$ is selected from the group consisting of (a) alkyl, (b) aryl, (c) hydrogen, and (d) arylalkyl; (23) —$(CH_2)_qCONR^BR^C$, where q is an integer from zero to four and where $R^B$ and $R^C$ are independently selected from the group consisting of (a) hydrogen, (b) alkyl, (c) aryl, and (d) arylalkyl; (24) —$(CH_2)_qSO_2R^D$, where q is an integer from zero to four and where $R^D$ is selected from the group consisting of (a) alkyl, (b) aryl, and (c) arylalkyl; (25) —$(CH_2)_qSO_2NR^ER^F$, where q is an integer from zero to four and where each of $R^E$ and $R^F$ is, independently, selected from the group consisting of (a) hydrogen, (b) alkyl, (c) aryl, and (d) arylalkyl; (26) thiol; (27) aryloxy; (28) cycloalkoxy; (29) arylalkoxy; (30) heterocyclylalkyl (e.g., heteroarylalkyl); (31) silyl; (32) cyano; and (33) —S(O)$R^H$ where $R^H$ is selected from the group consisting of (a) hydrogen, (b) alkyl, (c) aryl, and (d) arylalkyl. An unsubstituted aryl includes 6 to 14 carbon atoms (e.g., 6 to 10 carbon atoms). In some embodiments, each of these groups can be substituted with unsubstituted substituents as described herein for each respective group.

The term "aryl alkyl," as used herein, represents an alkyl group substituted with an aryl group. Each of the aryl and alkyl portions may be independently unsubstituted or substituted (e.g., optionally substituted aryl alkyl) as described for the individual groups.

The term "arylene," as used herein, refers to a divalent group that is aryl, as defined herein, in which one hydrogen atom is replaced with a valency. Arylene may be unsubstituted or substituted (e.g., optionally substituted arylene) as described for aryl.

The term "arylcarbonyl," as used herein, refers to a group —(CO)—R, where R is aryl. Arylcarbonyl may be unsubstituted or substituted (e.g., optionally substituted arylcarbonyl) as described herein for aryl.

The term "aryloxy," as used herein, refers to a group —OR, where R is aryl. Aryloxy may be unsubstituted or substituted (e.g., optionally substituted aryloxy) as described herein for aryl.

The term "aryloxy-carbonyl," as used herein, refers to a group —COOR, where R is aryl. Aryloxycarbonyl may be unsubstituted or substituted (e.g., optionally substituted aryloxycarbonyl) as described herein for aryl.

The term "arylsulfonate," as used herein, represents a group —S(O)$_2$—R, where R is aryl. Arylsulfonate may be unsubstituted or substituted (e.g., optionally substituted arylsulfonate) as described herein for aryl.

The term "aza," as used herein, represents a divalent —N(R$^{N1}$)— group or a trivalent —N= group. The aza group may be unsubstituted, where R$^{N1}$ is H or absent, or substituted, where R$^{N1}$ is as defined for "amino." Aza may also be referred to as "N," e.g., "optionally substituted N." Two aza groups may be connected to form "diaza."

The term "azido," as used herein, represents an N$_3$ group.

The term "carbamoyl," as used herein, refers to a group of formula RCOO—, where R is amino.

The term "carbocyclic," as used herein, represents an optionally substituted C$_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "cycloalkenyl," as used herein, refers to a non-aromatic carbocyclic group having from three to ten carbons (e.g., a C$_3$-C$_{10}$ cycloalkylene), unless otherwise specified. Non-limiting examples of cycloalkenyl include cycloprop-1-enyl, cycloprop-2-enyl, cyclobut-1-enyl, cyclobut-1-enyl, cyclobut-2-enyl, cyclopent-1-enyl, cyclopent-2-enyl, cyclopent-3-enyl, norbornen-1-yl, norbornen-2-yl, norbornen-5-yl, and norbornen-7-yl. The cycloalkenyl group may be unsubstituted or substituted (e.g., optionally substituted cycloalkenyl) as described for cycloalkyl.

The term "cycloalkenyl alkyl," as used herein, represents an alkyl group substituted with a cycloalkenyl group. Each of the cycloalkenyl and alkyl portions may be independently unsubstituted or substituted (e.g., optionally substituted cycloalkenyl alkyl) as described for the individual groups.

The term "cycloalkenylene," as used herein, refers to a divalent carbocyclic non-aromatic group having from three to ten carbons (e.g., C$_3$-C$_{10}$ cycloalkenylene), unless otherwise specified. Non-limiting examples of the cycloalkenylene include cycloprop-1-en-1,2-diyl; cycloprop-2-en-1,1-diyl; cycloprop-2-en-1,2-diyl; cyclobut-1-en-1,2-diyl; cyclobut-1-en-1,3-diyl; cyclobut-1-en-1,4-diyl; cyclobut-2-en-1,1-diyl; cyclobut-1-en-1,4-diyl; cyclopent-1-en-1,2-diyl; cyclopent-1-en-1,3-diyl; cyclopent-1-en-1,4-diyl; cyclopent-1-en-1,5-diyl; cyclopent-2-en-1,1-diyl; cyclopent-2-en-1,4-diyl; cyclopent-2-en-1,5-diyl; cyclopent-3-en-1,1-diyl; cyclopent-1,3-dien-1,2-diyl; cyclopent-1,3-dien-1,3-diyl; cyclopent-1,3-dien-1,4-diyl; cyclopent-1,3-dien-1,5-diyl; cyclopent-1,3-dien-5,5-diyl; norbornadien-1,2-diyl; norbornadien-1,3-diyl; norbornadien-1,4-diyl; norbornadien-1,7-diyl; norbornadien-2,3-diyl; norbornadien-2,5-diyl; norbornadien-2,6-diyl; norbornadien-2,7-diyl; and norbornadien-7,7-diyl. The cycloalkenylene may be unsubstituted or substituted (e.g., optionally substituted cycloalkenylene) as described for cycloalkyl.

The term "cycloalkyl," as used herein, refers to a cyclic alkyl group having from three to ten carbons (e.g., a C$_3$-C$_{10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo[2.2.1]heptyl, 2-bicyclo[2.2.1]heptyl, 5-bicyclo[2.2.1]heptyl, 7-bicyclo[2.2.1]heptyl, and decalinyl. The cycloalkyl group may be unsubstituted or substituted as defined herein (e.g., optionally substituted cycloalkyl). The cycloalkyl groups of this disclosure can be optionally substituted with: (1) acyl; (2) alkyl; (3) alkenyl; (4) alkynyl; (5) alkoxy; (6) alkylsulfinyl; (7) aryl; (8) amino; (9) arylalkyl; (10) azido; (11) cycloalkyl; (12) cycloalkylalkyl; (13) cycloalkenyl; (14) cycloalkenylalkyl; (15) halo; (16) heterocyclyl (e.g., heteroaryl); (17) (heterocyclyl)oxy; (18) (heterocyclyl)aza; (19) hydroxy; (20) nitro; (21) thioalkoxy; (22) —(CH$_2$)$_q$CO$_2$R$^A$, where q is an integer from zero to four, and R$^A$ is selected from the group consisting of (a) alkyl, (b) aryl, (c) hydrogen, and (d) arylalkyl; (23) —(CH$_2$)$_q$CONR$^B$R$^C$, where q is an integer from zero to four and where R$^B$ and R$^c$ are independently selected from the group consisting of (a) hydrogen, (b) alkyl, (c) aryl, and (d) arylalkyl; (24) —(CH$_2$)$_q$SO$_2$R$^D$, where q is an integer from zero to four and where R$^D$ is selected from the group consisting of (a) alkyl, (b) aryl, and (c) arylalkyl; (25) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) arylalkyl; (26) thiol; (27) aryloxy; (28) cycloalkoxy; (29) arylalkoxy; (30) heterocyclylalkyl (e.g., heteroarylalkyl); (31) silyl; (32) cyano; and (33) —S(O)R$^H$ where R$^H$ is selected from the group consisting of (a) hydrogen, (b) alkyl, (c) aryl, and (d) arylalkyl. In some embodiments, each of these groups can be substituted with unsubstituted substituents as described herein for each respective group.

The term "cycloalkylene," as used herein, refers to a divalent group that is cycloalkyl, as defined herein, in which one hydrogen atom is replaced with a valency. Cycloalkylene may be unsubstituted or substituted (e.g., optionally substituted cycloalkylene) as described for cycloalkyl.

The term "cycloalkyl alkyl," as used herein, represents an alkyl group substituted with a cycloalkyl group. Each of the cycloalkyl and alkyl portions may be independently unsubstituted or substituted (e.g., optionally substituted cycloalkyl alkyl) as described for the individual groups.

The term "dialkylamino," as used herein, represents a group —N(R$^{N1}$)$_2$, in which each RN' is independently alkyl. Dialkylamino may be optionally substituted; each alkyl in optionally substituted dialkylamino is independently and optionally substituted as described for alkyl.

The term "dialkylaminocarbonyl," as used herein, represents a chemical substituent of formula R—(CO)—, where R is dialkylamino.

The term "dialkylaminoalkylaminocarbonyl," as used herein, represents a chemical substituent of formula R$^1$—R$^2$—NH—(CO)—, where R$^1$ is dialkylamino, and R$^2$ is alkylene.

The term "halo," as used herein, represents a halogen selected from bromine, chlorine, iodine, and fluorine.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens, or, when the halogen group is F, haloalkyl group can be perfluoroalkyl. In some embodiments, the haloalkyl group can be further optionally substituted with 1, 2, 3, or 4 substituent groups as described herein for alkyl groups.

The term "heteroalkyl," as used herein refers to an alkyl, alkenyl, or alkynyl group interrupted once by one heteroatom; twice, each time, independently, by one heteroatom; three times, each time, independently, by one heteroatom; or four times, each time, independently, by one heteroatom. Each heteroatom is, independently, O, N, or S. In some embodiments, the heteroatom is O or N. An unsubstituted C$_{X-Y}$ heteroalkyl contains from X to Y carbon atoms as well as the heteroatoms as defined herein. The heteroalkyl group may be unsubstituted or substituted (e.g., optionally substituted heteroalkyl). When heteroalkyl is substituted and the substituent is bonded to the heteroatom, the substituent is selected according to the nature and valency of the heteroatom. Thus, the substituent, if present, bonded to the heteroatom, valency permitting, is selected from the group consisting of =O, —N(R$^{N2}$)$_2$, —SO$_2$OR$^{N3}$, —SO$_2$R$^{N2}$, —SOR$^{N3}$, —COOR$^{N3}$, an N-protecting group, alkyl, alkenyl, alkynyl, aryl, cycloalkyl, cycloalkenyl, cycloalkynyl, heterocyclyl, or cyano, where each R$^{N2}$ is independently H, alkyl, cycloalkyl, cycloalkenyl, cycloalkynyl, aryl, or heterocyclyl, and each R$^{N3}$ is independently alkyl, cycloalkyl, cycloalkenyl, cycloalkynyl, aryl, or heterocyclyl. Each of these substituents may itself be unsubstituted or substituted with unsubstituted substituent(s) defined herein for each respective group. When heteroalkyl is substituted and the substituent is bonded to carbon, the substituent is selected from those described for alkyl, provided that the substituent on the carbon atom bonded to the heteroatom is not CL, Br, or I. It is understood that carbon atoms are found at the termini of a heteroalkyl group.

The term "heteroaryl," as used herein, represents that subset of heterocyclyls, as defined herein, which include an aromatic ring system that contains at least one heteroatom. Thus, heteroaryls contain 4n+2 pi electrons within the mono- or multicyclic ring system. Heteroaryl can be unsubstituted or substituted (e.g., optionally substituted heteroaryl) with 1, 2, 3, or 4 substituents groups as defined for heterocyclyl.

The term "heteroarylcarbonyl," as used herein, refers to a group —(CO)—R, where R is heteroaryl. Heteroarylcarbonyl may be unsubstituted or substituted (e.g., optionally substituted heteroarylcarbonyl) as described herein for heterocyclyl.

The term "heteroaryloxy," as used herein, refers to a group —OR, where R is heteroaryl. Heteroaryloxy may be unsubstituted or substituted (e.g., optionally substituted heteroaryloxy) as described herein for heterocyclyl.

The term "heteroaryloxy-carbonyl," as used herein, refers to a group —COOR, where R is heteroaryl. Heteroaryloxycarbonyl may be unsubstituted or substituted (e.g., optionally substituted heteroaryloxycarbonyl) as described herein for heterocyclyl.

The term "heteroaryl alkyl," as used herein, represents an alkyl group substituted with a heteroaryl group. Thus, heteroaryl alkyl is a heterocyclyl alkyl group, in which the heterocyclyl includes at least one aromatic ring system including a heteroatom. Each of the heteroaryl and alkyl portions may be independently unsubstituted or substituted (e.g., optionally substituted heteroaryl alkyl) as described for the individual groups.

The term "heterocyclyl," as used herein, represents a 5-, 6-, or 7-membered ring or a fused ring system of two, three, or four rings, each of which is independently a 5-, 6-, or 7-membered ring, unless otherwise specified, provided that at least one of the rings contains one, two, three, or four heteroatoms independently selected from the group consisting of nitrogen, oxygen, and sulfur. The 5-membered ring has zero to two double bonds, and the 6- and 7-membered rings have zero to three double bonds. An unsubstituted heterocyclyl contains from one to twelve carbon atoms, unless specified otherwise. In some embodiments, an unsubstituted heterocyclyl contains at least two carbon atoms. In certain embodiments, an unsubstituted heterocyclyl contains up to nice carbon atoms. The fused "heterocyclyl" be a bridged multicyclic structure in which one or more carbons and/or heteroatoms bridges two non-adjacent members of a monocyclic ring, e.g., as found in a quinuclidinyl group. In some embodiments, the fused "heterocyclyl" includes bicyclic, tricyclic, and tetracyclic groups, in which at least one of the rings includes one or more heteroatoms as defined herein, and the remaining rings are carbocyclic rings, e.g., an aryl ring, a cyclohexane ring, a cyclohexene ring, a cyclopentane ring, a cyclopentene ring. Non-limiting examples of such fused heterocyclyls include indolyl, quinolyl, isoquinolyl, tetrahydroquinolyl, benzofuryl, benzothienyl, tropanes, and 1,2,3,5,8,8a-hexahydroindolizine. Non-limiting examples of heterocyclyls include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl (e.g., 1,3,4-thiadiazole), tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Still other exemplary heterocyclyls are: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl(e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3- diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Heterocyclic groups also include groups of the formula

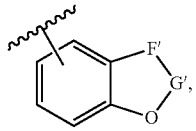

where
F' is selected from the group consisting of —CH$_2$—, —CH$_2$O— and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. Any of the heterocyclyl groups mentioned herein may be optionally substituted with one, two, three, four, or five substituents independently selected from the group consisting of: (1) acyl; (2) alkyl; (3) alkenyl; (4) alkynyl; (5) alkoxy; (6) alkylsulfinyl; (7) aryl; (8) amino; (9) arylalkyl; (10) azido; (11) cycloalkyl; (12) cycloalkylalkyl; (13) cycloalkenyl; (14) cycloalkenylalkyl; (15) halo; (16) heterocyclyl (e.g., heteroaryl); (17) (heterocyclyl)oxy; (18) (heterocyclyl)aza; (19) hydroxy; (20) oxo; (21) nitro; (22) sulfide; (23) thioalkoxy; (24) —(CH$_2$)$_q$CO$_2$R$^A$, where q is an integer from zero to four, and R$^A$ is selected from the group consisting of (a) alkyl, (b) aryl, (c) hydrogen, and (d) arylalkyl; (25) —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) arylalkyl; (26) —(CH$_2$)$_q$SO$_2$R$^D$, where q is an integer from zero to four and where R$^D$ is selected from the group consisting of (a) alkyl, (b) aryl, and (c) arylalkyl; (27) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) arylalkyl; (28) thiol; (29) aryloxy; (30) cycloalkoxy; (31) arylalkoxy; (31) heterocyclylalkyl (e.g., heteroarylalkyl); (32) silyl; (33) cyano; and (34) —S(O)R$^H$ where R$^H$ is selected from the group consisting of (a) hydrogen, (b) alkyl, (c) aryl, and (d) arylalkyl. In some embodiments, each of these groups can be independently unsubstituted or substituted with unsubstituted substituent(s) as described herein for each of the recited groups. For example, the alkylene group of an aryl-C$_1$-alkylene or a heterocyclyl-C$_1$-alkylene can be further substituted with an oxo group to afford the respective aryloyl and (heterocyclyl)oyl substituent group.

The term "heterocyclyl alkyl," as used herein, represents an alkyl group substituted with a heterocyclyl group. Each of the heterocyclyl and alkyl portions may be independently unsubstituted or substituted (e.g., optionally substituted heterocyclyl alkyl) as described for the individual groups.

The term "heterocyclylene," as used herein, refers to a divalent group that is heterocyclyl, as defined herein, in which one hydrogen atom is replaced with a valency. Heterocyclylene may be unsubstituted or substituted (e.g., optionally substituted heterocyclylene) as described for heterocyclyl.

The terms "hydroxyl" and "hydroxy," as used interchangeably herein, represent an —OH group.

The term "internucleoside," as used herein, refers to a position within an oligonucleotide that is disposed between two contiguous nucleosides, one nucleoside and an adjacent abasic spacer, or two contiguous abasic spacers.

The term "n-membered ring," as used herein, represents a cycloalkylene, arylene, or heterocyclylene having n atoms in a ring bearing both valencies. The n-membered rings can be unsubstituted or substituted (e.g., optionally substituted n-membered ring) as described herein for cycloalkyl, when n-membered ring is cycloalkylene, for aryl, when n-membered ring is arylene, or for heterocyclyl, when n-membered ring is heterocyclylene.

The term "nitro," as used herein, represents an —NO$_2$ group.

The term "nucleobase," as used herein, represents a nitrogen-containing heterocyclic ring found at the 1' position of the sugar moiety of a nucleotide or nucleoside. Nucleobases can be unmodified or modified. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; those disclosed in *The Concise Encyclopedia Of Polymer Science And Engineering*, pages 858-859, Kroschwitz, J. I., ed. John Wiley & Sons, 1990; those disclosed by Englisch et al., *Angewandte Chemie, International Edition*, 1991, 30, 613; and those disclosed by Sanghvi, Y. S., Chapter 15, *Antisense Research and Applications*, pages 289 302, (Crooke et al., ed., CRC Press, 1993). Nucleobases can be 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications 1993, CRC Press, Boca Raton, pages 276-278). These may be combined, in particular embodiments, with 2'-O-methoxyethyl sugar modifications. United States patents that teach the preparation of certain of these modified nucleobases as well as other modified nucleobases include, but are not limited to, the above noted U.S. Pat. Nos. 3,687,808; 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,594,121; 5,596,091; 5,614,617; and 5,681,941. For the purposes of this disclosure, "modified nucleobases," as used herein, further represents nucleobases, natural or non-natural, which include one or more protecting groups as described herein.

The term "nucleoside," as used herein, represents a sugar-nucleobase combination. Nucleoside, as used herein, is a compound, a monovalent group, or a divalent group. The sugar is: ribose, modified ribose (e.g., 2'-deoxyribose), mannose, arabinose, glucopyranose, galactopyranose, 4-thioribose, a morpholino sugar (as found in morpholino oligonucleotides), threose (as found in threose nucleic acids), propanediol (as found in glycol nucleic acids), or a locked nucleic acid (e.g., ribose that is modified to include a bridge (e.g., a —$CH_2$—O-bridge), e.g., connecting 4' and 2' carbon atoms of the ribose). The sugar can be an L-sugar or D-sugar. A modified ribose has a substitution at position 2' with H, OR, R, halo (e.g., F), SH, SR, $NH_2$, NHR, $NR_2$, or CN, where R is an optionally substituted $C_{1-6}$ alkyl (e.g., ($C_{1-6}$ alkoxy)-$C_{1-6}$-alkyl) or optionally substituted ($C_{6-14}$ aryl)-$C_{1-4}$-alkyl. In some embodiments, the term "nucleoside" refers to a group having the following structure:

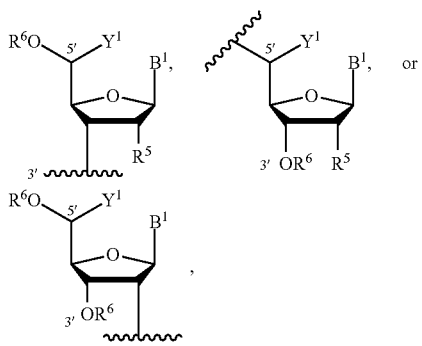

in which $B^1$ is a nucleobase; $R^5$ is H, halogen (e.g., F), O-protected hydroxyl, or optionally substituted $C_{1-6}$ alkoxy (e.g., methoxy or methoxyethoxy); $Y^1$ is H or $C_{1-6}$ alkyl (e.g., methyl); $R^6$ is H or a hydroxyl protecting group; and each of 3' and 5' indicate the position of a bond to another group. In some embodiments, the nucleoside is a locked nucleic acid (LNA). Locked nucleosides are known in the art and are described, for example, in U.S. Pat. Nos. 6,794,499; 7,084,125; and 7,053,207. In certain embodiments, the nucleoside is a locked nucleic acid having the following structure:

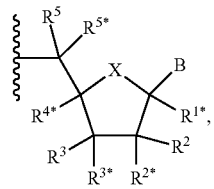

in which
X is —O—, —S—, —N($R^{N*}$)—, —C($R^8R^{6*}$)—, —O—C($R^7R^{7*}$)—, —C($R^6R^{6*}$)—O—, —S—C($R^7R^{7*}$)—, —C($R^6R^{6*}$)—S—, —N(RN*)—C($R^7R^{7*}$)—, —C($R^6R^{6*}$)—N(RN*)—, or —C($R^6R^{6*}$)—C($R^7R^{7*}$)—;
B is a nucleobase;
$R^{3*}$ is a valency or $OR^A$, where $R^A$ is H or a hydroxyl protecting group;
one or two pairs of non-geminal substituents selected from the group consisting of $R^{1*}$, $R^{4*}$, $R^5$, $R^{5*}$, $R^6$, $R^{6*}$, $R^7$, $R^{7*}$, RN*, $R^2$, $R^{2*}$, and $R^3$ combine to form one or two biradicals, respectively, where each biradical independently consists of 1-8 groups independently selected from the group consisting of —C($R^aR^b$)—, —C($R^a$)=C($R^a$)—, —C($R^a$)=N—, —O—, —Si($R^a$)$_2$—, —S—, —$SO_2$—, —N($R^a$)—, and >C=Z, where Z is selected from =O—, =S—, =N($R^a$), and =$CH_2$, and each $R^a$ and each $R^b$ is independently hydrogen, optionally substituted $C_{1-12}$ alkyl, optionally substituted $C_{2-12}$ alkenyl, optionally substituted $C_{2-12}$ alkynyl, —OH, $C_{1-12}$-alkoxy, $C_{2-12}$ alkenyloxy, —COOH, $C_{1-12}$ alkoxycarbonyl, optionally substituted aryl, optionally substituted aryloyl, optionally substituted aryloxy-carbonyl, optionally substituted aryloxy, optionally substituted heteroaryl, optionally substituted heteroaryloyl, optionally substituted heteroaryloxy-carbonyl, optionally substituted heteroaryloxy, amino, ($C_{1-6}$-alkyl)amino, di($C_{1-6}$-alkyl)amino, carbamoyl, ($C_{1-6}$-alkyl)-amino-carbonyl, di($C_{1-6}$-alkyl)-amino-carbonyl, amino-1-6-alkyl-aminocarbonyl, ($C_{1-6}$-alkyl)amino-1-6-alkyl-aminocarbonyl, di($C_{1-6}$-alkyl)amino-$C_{1-6}$-alkyl-aminocarbonyl, —$NHCONH_2$, $C_{2-7}$-alkanoylamino, $C_{1-6}$ alkanoyloxy, alkylsulfonyl, $C_{1-6}$ alkylsulphonyloxy, nitro, azido, —SH, $C_{1-6}$ thioalkyl, or halo; and
each of the remaining substituents $R^{1*}$, $R^2$, $R^{2*}$, $R^3$, $R^{4*}$, $R^5$, $R^{5*}$, $R^6$, $R^{6*}$, $R^7$, and $R^{7*}$ is independently hydrogen, optionally substituted $C_{1-12}$ alkyl, optionally substituted $C_{2-12}$ alkenyl, optionally substituted $C_{2-12}$ alkynyl, hydroxy, $C_{1-12}$ alkoxy, $C_{2-12}$ alkenyloxy, —COOH, $C_{1-12}$ alkoxycarbonyl, $C_{1-12}$ alkanoyl, formyl, optionally substituted aryl, optionally substituted aryloxy-carbonyl, optionally substituted aryloxy, optionally substituted arylcarbonyl, optionally substituted heteroaryl, optionally substituted heteroaryloxy-carbonyl, optionally substituted heteroaryloxy, optionally substituted heteroarylcarbonyl, amino, (1-6-alkyl)amino, di($C_{1-6}$-alkyl)amino, carbamoyl, ($C_{1-6}$-alkyl)-amino-carbonyl, di($C_{1-6}$-alkyl)-amino-carbonyl, amino-1-6-alkyl-aminocarbonyl, ($C_{1-6}$-alkyl)amino-1-6-alkyl-aminocarbonyl, di($C_{1-6}$-alkyl)amino-$C_{1-6}$-alkyl-aminocarbonyl, $C_{1-6}$ alkanoylamino, $C_{1-6}$ alkanoyloxy, $C_{1-6}$ alkylsulfonyl, $C_{1-6}$ alkylsulfonyloxy, nitro, azido, —SH, $C_{1-6}$-thioalkyl, or halogen; or two remaining geminal substituents may combine to form =O, =S, =$NR^a$, =$CH_2$, or a 1-5 carbon atom(s) alkylene chain which is optionally interrupted one or two heteroatoms independently selected from the group consisting of —O—, —S—, and —(NR$^N$)—, where R$^N$ is hydrogen or 014-alkyl; or two remaining vicinal substituents combine to form an additional bond resulting in a double bond; and R$^{N*}$, when present and not involved in the biradical, is hydrogen or 014-alkyl.

In particular embodiments, the locked nucleic acid has the following structure:

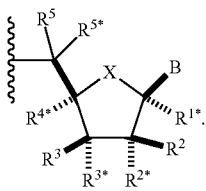

In further embodiments, X is —O— and B is a nucleobase. In some embodiments,

R$^{3*}$ is a valency or OR$^A$, where R$^A$ is H or a hydroxyl protecting group;

R$^{2*}$ and R$^{4*}$ combine to form a biradical consisting of 2-5 groups/atoms selected from —(CR*R*)$_r$—Y—(CR*R*)$_s$—, —(CR*R*)$_s$—, —(CR*R*)$_r$—Y—(CR*R*)$_s$—Y—, —Y—(CR*R*)$_{r+s}$—Y—, —Y—(CR*R*)$_r$—Y—(CR*R*)$_s$—, —(CR*R*)$_{r+s}$—, each R* is independently hydrogen, halogen, —OH, —SH, amino, optionally substituted C$_{1-6}$-alkoxy, optionally substituted C$_{1-6}$ alkyl, where Y is —O—, —S—, absent, or —N(R$^N$)—, and each of r and s is an integer from 0 to 4, provided that the sum r+s is 1-4, and provided that, when the biradical is —(CR*R*)$_r$—Y—(CR*R*)$_s$—, then Y is —S— or —N(R$^N$)—; and each of the substituents R$^{1*}$, R$^2$, R$^3$, R$^5$, and R$^{5*}$ is independently hydrogen, optionally substituted C$_{1-12}$ alkyl, optionally substituted C$_{2-12}$ alkenyl, optionally substituted C$_{2-12}$ alkynyl, —OH, C$_{1-12}$ alkoxy, C$_{2-12}$ alkenyloxy, —COOH, C$_{1-12}$ alkoxycarbonyl, C$_{1-12}$ alkanoyl, optionally substituted aryl, optionally substituted aryloxy-carbonyl, optionally substituted aryloxy, optionally substituted aryloyl, optionally substituted heteroaryl, optionally substituted heteroaryloxy-carbonyl, optionally substituted heteroaryloxy, optionally substituted heteroaryloyl, amino, (C$_{1-6}$-alkyl)amino, di(C$_{1-6}$-alkyl)amino, carbamoyl, (C$_{1-6}$-alkyl)-amino-carbonyl, di(C$_{1-6}$-alkyl)-amino-carbonyl, amino-C$_{1-6}$-alkyl-aminocarbonyl, (C$_{1-6}$-alkyl)amino-C$_{1-6}$-alkyl-aminocarbonyl, di(C$_{1-6}$-alkyl)amino-C$_{1-6}$-alkyl-aminocarbonyl, —NHCONH$_2$, C$_{2-7}$-alkanoylamino, C$_{1-6}$ alkanoyloxy, alkylsulfonyl, C$_{1-6}$ alkylsulphonyloxy, nitro, azido, —SH, C$_{1-6}$ thioalkyl, or halo.

The term "nucleotide," as used herein, represents a nucleoside bonded to a phosphate, phosphorothioate, phosphorodithioate, phosphonate, or phosphoramidate.

The term "oligonucleotide," as used herein, represents a compound containing nucleosides and optionally abasic spacers covalently linked to each other through internucleoside bridging groups, e.g., phosphates, phosphorothioates, phoshorodithioates, phosphites, phosphonates, and phosphoramidates. An oligonucleotide includes a total of 2-100 nucleosides and abasic spacers, provided that the oligonucleotide includes at least one nucleoside. In some embodiments, an oligonucleotide includes 1-6 (e.g., 1, 2, or 3) abasic spacers.

The terms "oxa" and "oxy," as used interchangeably herein, represents a divalent oxygen atom that is connected to two groups (e.g., the structure of oxy may be shown as —O—).

The term "oxo," as used herein, represents a divalent oxygen atom that is connected to one group (e.g., the structure of oxo may be shown as =O).

The term "pseudohalogen," as used herein, represents an optionally substituted alkylsulfonate or optionally substituted arylsulfonate. Non-limiting examples of pseudohalogens include methanesulfonate, trifluoromethanesulfonate, benzenesulfonate, and p-toluenesulfonate.

The term "protecting group," as used herein, represents a group intended to protect a functional group (e.g., a hydroxyl, an amino, or a carbonyl) from participating in one or more undesirable reactions during chemical synthesis (e.g., polynucleotide synthesis). The term "O-protecting group," as used herein, represents a group intended to protect an oxygen containing (e.g., phenol, hydroxyl or carbonyl) group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used 0- and N-protecting groups are disclosed in Greene, "Protective Groups in Organic Synthesis," 3$^{rd}$ Edition (John Wiley & Sons, New York, 1999), which is incorporated herein by reference. Exemplary 0- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl. N-protecting groups useful for protection of amines in nucleobases include phenoxyacetyl and (4-isopropyl)phenoxyacetyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and arylalkyl ethers (e.g., trityl; methylthiomethyl; methoxymethyl; benzyloxymethyl; siloxymethyl; 2,2,2-trichloroethoxymethyl; tetrahydropyranyl; tetrahydrofuranyl; ethoxyethyl; 1-[2-(trimethylsilyl) ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2, 2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p- biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropoxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), benzyloxycarbonyl (Cbz), phenoxyacetyl, and (4-isopropyl)phenoxyacetyl.

The term "silyl," as used herein, refers to a group of formula —SiR$_3$, where each R is independently alkyl, alkenyl, aryl, or arylalkyl. Silyl can be optionally substituted in the same manner as defined for each R group.

The term "sugar analogue," as used herein, represents a $C_{3-6}$ monosaccharide or $C_{3-6}$ alditol (e.g., glycerol), which is modified to replace one hydroxyl group with a bond to an oxygen atom in formula (IIIA), (IIIB), (IIIC), or (IIID) (e.g., in formula (IVA), (IVB), (IVC), (IVD), (IVA'), (IVB'), (IVC'), (IVD'), (IVA''), (IVB''), (IVC''), or (IVD'')). A sugar analogue does not contain a nucleobase capable of engaging in hydrogen bonding with a nucleobase in a complementary strand. A sugar analogue is cyclic or acyclic. Further optional modifications included in a sugar analogue are: a replacement of one, two, or three of the remaining hydroxyl groups or carbon-bonded hydrogen atoms with H; optionally substituted $C_{1-6}$ alkyl; —(CH$_2$)$_{t1}$—OR$^Z$, where t1 is an integer from 1 to 6, and R$^Z$ is optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted ($C_{1-9}$ heterocyclyl)-$C_{1-6}$-alkyl, optionally substituted ($C_{6-10}$ aryl)-$C_{1-6}$-alkyl, or optionally substituted ($C_{3-8}$ cycloalkyl)-$C_{1-6}$-alkyl; introduction of one or two unsaturation(s) (e.g., one or two double bonds); and replacement of one, two, or three hydrogens or hydroxyl groups with substituents as defined for alkyl, alkenyl, cycloalkyl, cycloalkenyl, or heterocyclyl. Non-limiting examples of sugar analogues are optionally substituted $C_{2-6}$ alkyl, optionally substituted $C_{2-6}$ alkenyl, optionally substituted $C_5$ cycloalkyl, optionally substituted $C_5$ cycloalkenyl, optionally substituted heterocyclyl (e.g., optionally substituted pyrrolidinyl, optionally substituted tetrahydrofuranyl, or optionally substituted tetrahydrothiophenyl), optionally substituted ($C_{1-9}$ heterocyclyl)-$C_{1-6}$-alkyl, or optionally substituted ($C_{3-8}$ cycloalkyl)-$C_{1-6}$-alkyl.

The term "stereochemically enriched," as used herein, refers to a local stereochemical preference for one enantiomer of the recited group over the opposite enantiomer of the same group. Thus, a, oligonucleotide containing a stereochemically enriched phosphorothioate is an oligonucleotide, in which a phosphorothioate of predetermined stereochemistry is present in preference to a phosphorothioate of stereochemistry that is opposite of the predetermined stereochemistry. This preference can be expressed numerically using a diastereomeric ratio (dr) for the phosphorothioate of the predetermined stereochemistry. The diastereomeric ratio for the phosphorothioate of the predetermined stereochemistry is the molar ratio of the diastereomers having the identified phosphorothioate with the predetermined stereochemistry relative to the diastereomers having the identified phosphorothioate with the stereochemistry that is opposite of the predetermined stereochemistry. The diastereomeric ratio for the phosphorothioate of the predetermined stereochemistry may be 75:25 or greater (e.g., 80:20 or greater, 90:10 or greater, 95:5 or, or 98:2 or greater).

The term "sulfide," as used herein, represents —S— or =S.

The term "thioalkyl," as used herein, refers to a divalent group —SR, in which R is alkyl. Thioalkyl may be unsubstituted or substituted (e.g., optionally substituted thioalkyl) as described for alkyl.

The term "thiocarbonyl," as used herein, represents a C(=S) group. Non-limiting example of functional groups containing a "thiocarbonyl" includes thioesters, thioketones, thioaldehydes, thioanhydrides, thioacyl chlorides, thioamides, thiocarboxylic acids, and thiocarboxylates.

The term "thioheterocyclylene," as used herein, represents a divalent group —S—R'—, where R' is a heterocyclylene as defined herein.

The term "thiol," as used herein, represents an —SH group.

One of skill in the art will recognize that references P-stereogenic groups, compounds containing them, and diastereoselective syntheses utilizing the same are for enantioenriched and diastereoenriched compositions of the compounds (e.g., enantiomeric ratio of 90:10 or greater (e.g., 95:5 or greater or 98:2 or greater)), where the major stereoisomer is that which is identified either by a structure or by a stereochemical identifier, such as (S) or (R) for the carbon stereocenters and (S$_P$) or (R$_P$) for the phosphorus stereocenters.

DETAILED DESCRIPTION

The invention provides P-stereogenic groups for diastereoselective synthesis of stereochemically enriched P-stereogenic compounds. P-stereogenic groups of the invention can be used in highly diastereoselective synthesis of P-stereogenic phosphorothioates (e.g., with dr of 90:10 or greater (e.g., 95:5 or greater or 98:2 or greater)). Advantageously, P-stereogenic groups (e.g., those having R$^3$ and R$^4$ be H)) can be readily accessed through a short (e.g., a two-step synthesis) from commercially available materials. A P-stereogenic group of the invention is a group of formula (IA), (IB), (IC), or (ID):

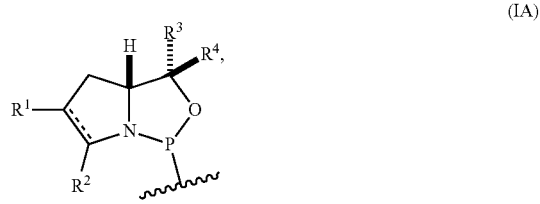

(IA)

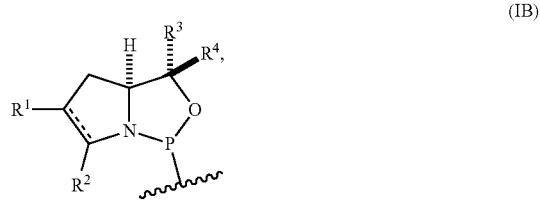

(IB)

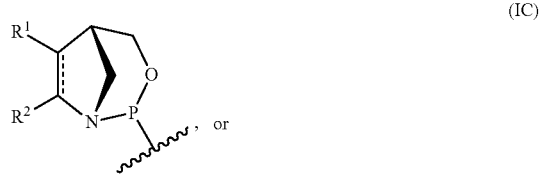

(IC)

or

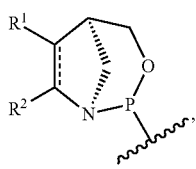
(ID)

where
=== is a single carbon-carbon bond or a double carbon-carbon bond;
each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and
each of $R^3$ and $R^4$ is independently H, optionally substituted $C_{1-6}$ alkyl, or optionally substituted $C_{6-10}$ aryl.

In some embodiments, the P-stereogenic group is a group of formula (IA) or (IB).

In certain embodiments, the P-stereogenic group is of the following structure:

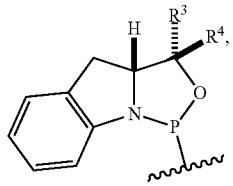
(IIA)

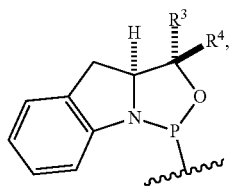
(IIB)

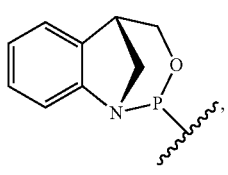
(IIC)

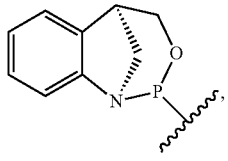
(IID)

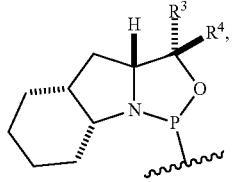
(IIA')

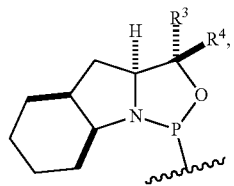
(IIB')

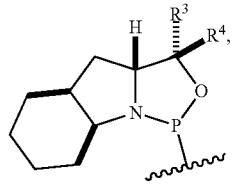
(IIC')

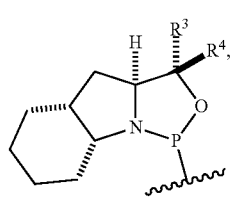
(IID')

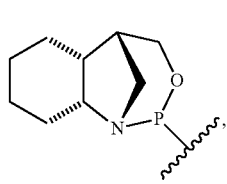
(IIA")

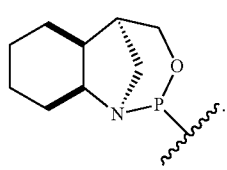
(IIB")

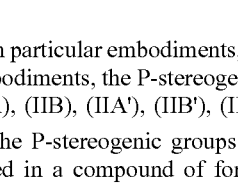
(IIC"), or

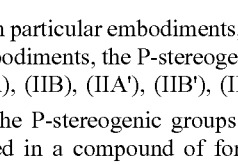
(IID").

In particular embodiments, $R^3$ and $R^4$ are each H. In some embodiments, the P-stereogenic group is a group of formula (IIA), (IIB), (IIA'), (IIB'), (IIA"), or (IIB").

The P-stereogenic groups of the invention may be provided in a compound of formula (IIIA), (IIIB), (IIIC), or (IIID):

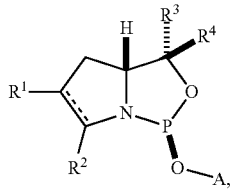
(IIIA)

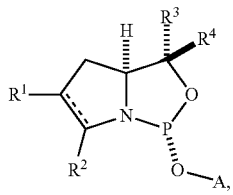
(IIIB)

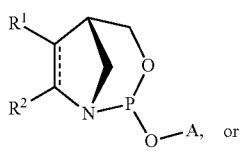
(IIIC)

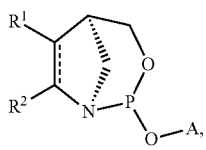
(IIID)

wherein
- ═ is a single carbon-carbon bond or a double carbon-carbon bond;
- A is an optionally substituted $C_{1-12}$ alkyl, optionally substituted $C_{3-10}$ cycloalkyl, optionally substituted $C_{3-10}$ cycloalkyl-$C_{1-6}$-alkyl, optionally substituted $C_{1-9}$ heterocyclyl, optionally substituted $C_{1-9}$ heterocyclyl-$C_{1-6}$-alkyl, sugar analogue, nucleoside, nucleotide, or oligonucleotide;
- each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and
- each of $R^3$ and $R^4$ is independently H, optionally substituted $C_{1-6}$ alkyl, or optionally substituted $C_{6-10}$ aryl.

In certain embodiments, the P-stereogenic group is of formula (IIIC') or (IIID'):

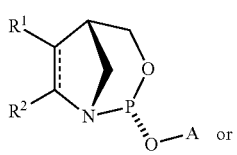
(IIIC')

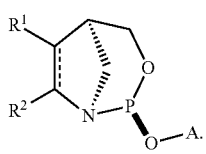
(IIID')

In certain embodiments, the compound is of the following structure:

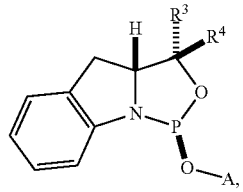
(IVA)

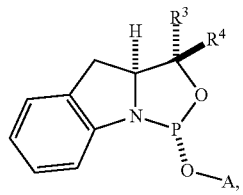
(IVB)

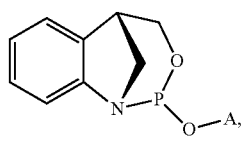
(IVC)

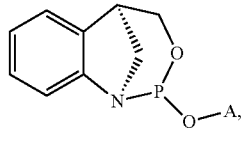
(IVD)

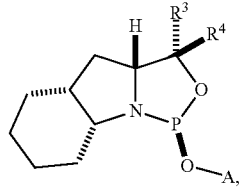
(IVA')

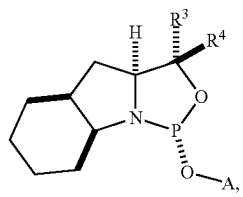
(IVB')

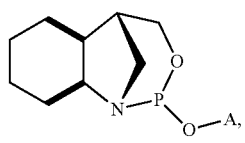
(IVC')

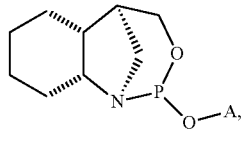
(IVD')

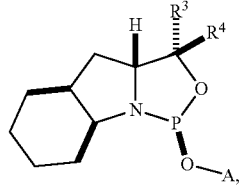
(IVA")

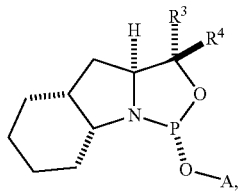
(IVB″)

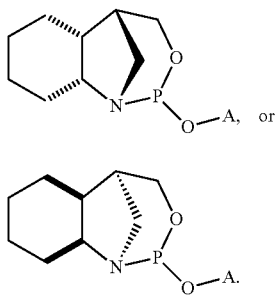
(IVC″)

(IVD″)
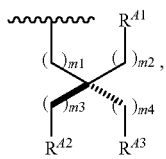

In particular embodiments, A is an optionally substituted $C_{1-12}$ alkyl, optionally substituted $C_{3-10}$ cycloalkyl, optionally substituted $C_{3-10}$ cycloalkyl-$C_{1-6}$-alkyl, optionally substituted $C_{1-9}$ heterocyclyl, optionally substituted $C_{1-9}$ heterocyclyl-$C_{1-6}$-alkyl, or sugar analogue.

In further embodiments, A is a group of formula (X):

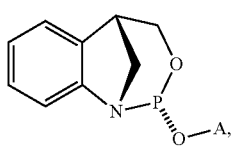
(X)

where each of $R^{A1}$, $R^{A2}$, and $R^{A3}$ is independently H, —$OR^{A4}$, or —$N(R^{A4})(R^{A5})$; where $R^{A4}$ is optionally substituted $C_{1-16}$ alkyl, optionally substituted $C_{2-16}$ heteroalkyl, or a protecting group, and $R^{A5}$ is H optionally substituted $C_{1-16}$ alkyl, optionally substituted $C_{2-16}$ heteroalkyl, or a protecting group; and each of m1, m2, m3, and m4 is independently an integer from 0 to 11, provided that the quaternary carbon in the structure above is bonded to 0 or 1 atoms other than carbon and hydrogen, and provided that the sum of m1, m2, m3 and m4 is 11 or less.

In some embodiments, the compound is of formula (IVA), (IVB), (IVA'), (IVB'), (IVA″), or (IVB″). In other embodiments, the phosphoramidite is of formula (IVE), (IVF), (IVE'), (IVF'), (IVE″), or (IVF″):

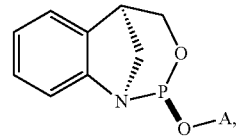
(IVE)

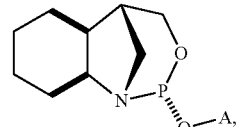
(IVF)

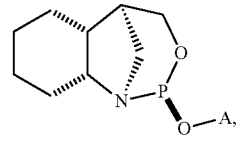
(IVE')

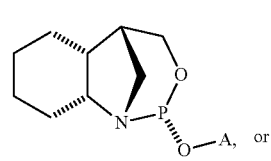
(IVF')

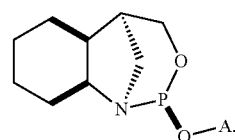
(IVE″)

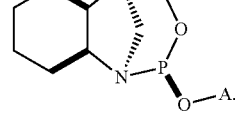
(IVF″)

In certain embodiments, P-stereogenic groups may be provided in nucleoside phosphoramidites. The nucleoside phosphoramidites of the invention can be used to prepare oligonucleotides having P-stereogenic phosphorothioates with high diastereoselectivity (e.g., with dr of 90:10 or greater (e.g., 95:5 or greater or 98:2 or greater)). Advantageously, nucleoside phosphoramidites of the invention (e.g., those having $R^3$ and $R^4$ be H) can be readily accessed through a short synthesis (e.g., a two-step synthesis) from commercially available materials. Accordingly, the nucleoside phosphoramidites of the invention are a practical solution for high-yield synthesis of oligonucleotides having stereochemically enriched P-stereogenic phosphorothioates.

The nucleoside phosphoramidites of the invention include a sugar bonded to a nucleobase and to a phosphoramidite of the following structure:

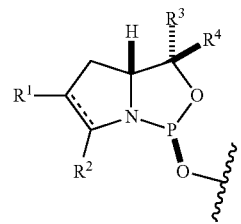
(VA)

(VB)

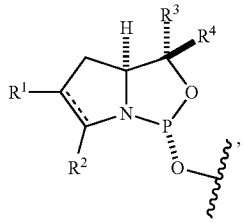

(VC)

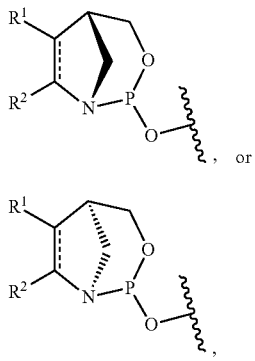, or (VD)

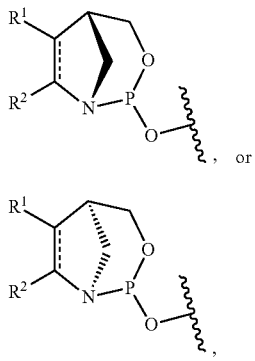, where
== is a single carbon-carbon bond or a double carbon-carbon bond;
each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and
each of $R^3$ and $R^4$ is independently H, optionally substituted $C_{1-6}$ alkyl, or optionally substituted $C_{6-10}$ aryl.

In certain embodiments, the phosphoramidite is of formula (VA) or (VB). In particular embodiments, the phosphoramidite is of formula (VC') or (VD'):

(VC')

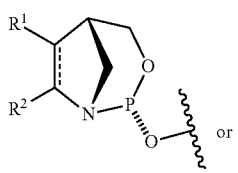 or (VD')

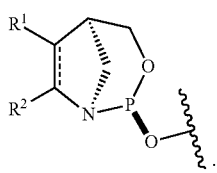.

In some embodiments, the nucleoside phosphoramidite is of the following structure:

(VIA)

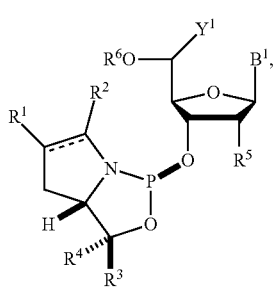

(VIB)

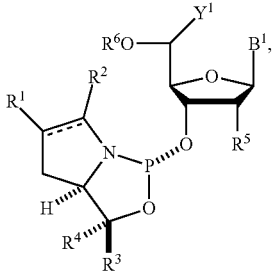, (VIC)

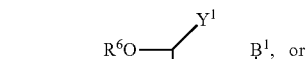, or (VID)

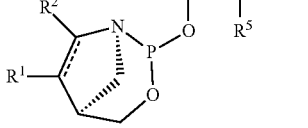, where
$B^1$ is a nucleobase;
$Y^1$ is H or $C_{1-6}$ alkyl (e.g., methyl);
$R^5$ is H, O-protected hydroxyl, optionally substituted $C_{1-6}$ alkoxy, or halogen (e.g., F); and
$R^6$ is a hydroxyl protecting group;
and the remaining variables are as defined for formulas (VA), (VB), (VC), and (VD).

In particular embodiments, the nucleoside phosphoramidite is of formula (VIC') or (VID'):

(VIC')

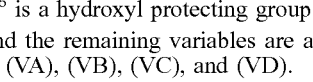 or (VID')

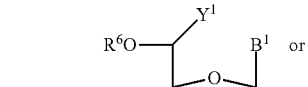.

In certain embodiments, the phosphoramidite is of the following structure:

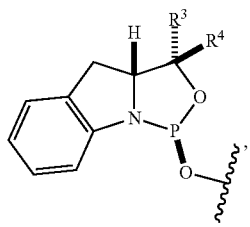
(VIIA)
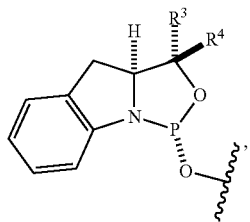
(VIIB)
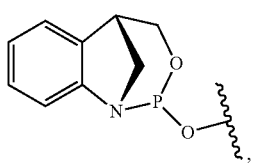
(VIIC)
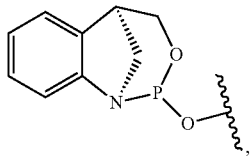
(VIID)
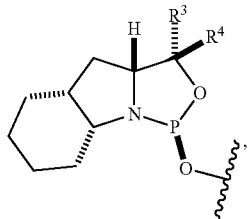
(VIIA')
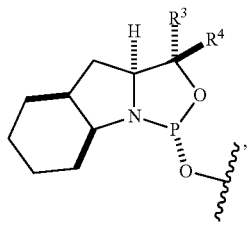
(VIIB')
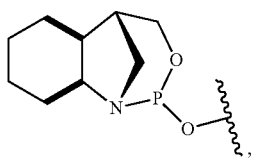
(VIIC')
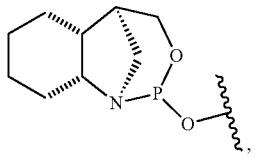
(VIID')
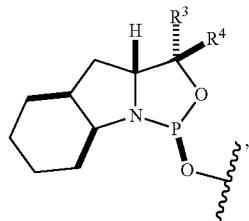
(VIIA")
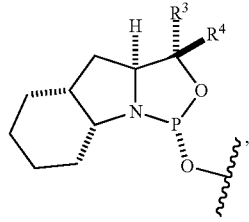
(VIIB")
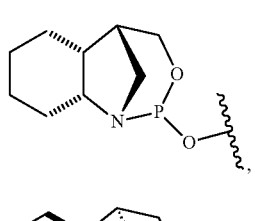
(VIIC")
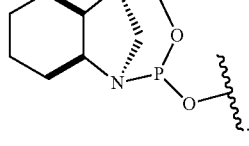
(VIID")
In particular embodiments, $R^3$ and $R^4$ are each H. In some embodiments, the phosphoramidite is of formula (VIIA), (VIIB), (VIIA'), or (VIIB'). In other embodiments, the phosphoramidite is of formula (VIIE), (VIIF), (VIIE'), (VIIF'), (VIIE"), or (VIIF"):
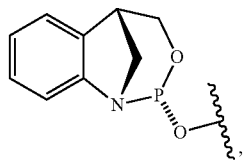
(VIIE)
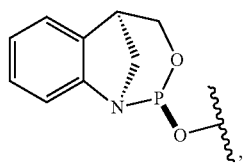
(VIIF)
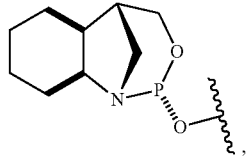
(VIIE')
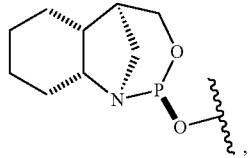
(VIIF')

-continued

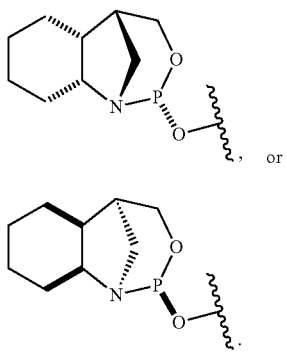
(VIIE″), or

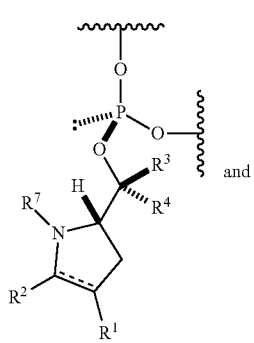
(VIIF″).

Diasteroselective Preparation of Oligonucleotides Containing Phosphorothioate Phosphodiester The nucleoside phosphoramidites of the invention may be used for the diastereoselective preparation of oligonucleotides containing a phosphorothioate phosphodiester using reaction conditions known in the art for the phosphoramidite route for oligonucleotide synthesis.

Typically, a nucleoside phosphoramidite of formula (VA) produces an internucleoside ($R_P$)-phosphorothioate, and a nucleoside phosphoramidite of formula (VB) produces an internucleoside ($S_P$)-phosphorothioate.

In a typical oligonucleotide chain growth step, a nucleoside phosphoramidite of the invention is coupled to a nucleoside having a 5'-hydroxyl (e.g., a nucleoside linked to a solid support) or an oligonucleotide having a 5'-hydroxyl (e.g., an oligonucleotide linked to a solid support) to produce a product oligonucleotide including an internucleoside phosphite substituted with a ring-opened chiral auxiliary. Typically, the coupling step is performed in the presence of a coupling activator. Coupling activators are known in the art; non-limiting examples of coupling activators are (benzylthio)-1H-tetrazole (BTT), N-phenylimidazolium trifluoromethanesulfonate (PhIMT), 1-(cyanomethyl)pyrrolidinium trifluoromethanesulfonate (CMPT), 1,8-diazabicyclo[5.4.0]undec-7-ene (DBU), 4,5-dicyanoimidazole (DCI), 4,5-dichloroimidazole, benzimidazolium trifluoromethanesulfonate (BIT), benzotriazole, 3-nitro-1,2,4-triazole (NT), tetrazole, (ethylthio)-1H-tetrazole (ETT), (4-nitrophenyl)-1H-tetrazole, 1-(cyanomethyl)piperidinium trifluoromethanesulfonate, and N-cyanomethyldimethylammonium trifluoromethanesulfonate. In certain embodiments (e.g., when the nucleoside phosphoramidite includes 2'-deoxyribose), the coupling activator is preferably CMPT. The product oligonucleotide may be an oligonucleotide (e.g., an oligonucleotide having a total of 2-100 nucleosides (e.g., 2 to 50 or 2 to 35) including one or more (e.g., 1 to 6, 1 to 5, 1 to 4, 1 to 3, 1 to 2, or 1) internucleoside groups independently selected from the group consisting of linkers of formula (XIA) and (XIB):

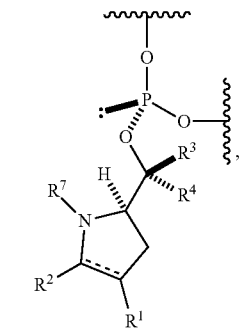
(XIA) and

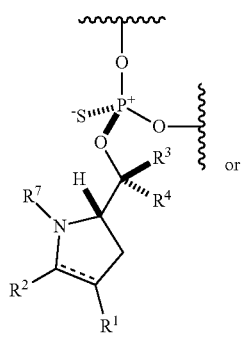
(XIB), where
== is a single carbon-carbon bond or a double carbon-carbon bond;
each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring;
each of $R^3$ and $R^4$ is independently H, optionally substituted $C_{1-6}$ alkyl, or optionally substituted $C_{6-10}$ aryl; and
$R^7$ is acyl (e.g., alkanoyl).

The oligonucleotides including one or more internucleoside groups of formula (XIA) and/or (XIB) may be intermediates in the synthesis of an oligonucleotide including at least one stereochemically enriched internucleoside phosphorothioate. For example, these oligonucleotides may be subjected to a sulfurization reaction with a sulfurizing agent (e.g., Beaucage reagent; 3-((N,N-dimethylaminomethylidene)amino)-3H-1,2,4-dithiazole-5-thione (DDTT); $S_8$; or a compound of formula (XA) or (XB)) to produce an oligonucleotide (e.g., an oligonucleotide having a total of 2-100 nucleosides (e.g., 2 to 50 or 2 to 35) including one or more (e.g., 1 to 6, 1 to 5, 1 to 4, 1 to 3, 1 to 2, or 1) internucleoside groups independently selected from the group consisting of linkers of formula (XIIA) and (XIIB):

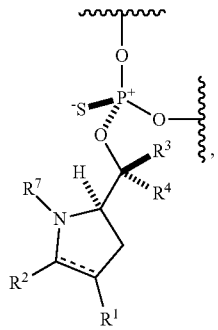
(XIIA) or (XIIB), where the variables are as describe for formulae (XIA) and (XIB).

Sulfurizing agents are known in the art; non-limiting examples of the sulfurizing agents are Beaucage reagent; 3-((N,N-dimethylaminomethylidene)amino)-3H-1,2,4-dithiazole-5-thione (DDTT); $S_8$; and compounds of formula (XA) and (XB).

The compound of formula (XA) is of the following structure:

$$R^8\text{—}S\text{—}S\text{—}R^8, \quad (XA)$$

or a salt thereof,
where
each $R^8$ is independently $R^9C(X^1)\text{—}$, $(R^{10})_2P(X^1)$ or $R^{11}S(O)_2\text{—}$, where each $R^9$ is independently alkylamino or dialkylamino; each $R^{10}$ is independently alkoxy or aryloxy; each $R^{11}$ is independently hydroxyl, alkyl, aryl, or heteroaryl; and $X^1$ is =O or =S.

The compound of formula (XB) is of the following structure:

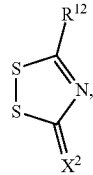

(XB)

where
$X^2$ is O or S; and
$R^{12}$ is aryl, amino, or alkoxy.

For example, the compound of formula (XB) can be:

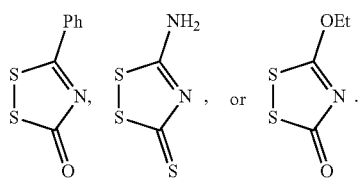

The oligonucleotide including one or more internucleoside groups of formula (XIIA) and/or (XIIB) is then fed back into the synthesis, e.g., by deprotecting the 5'-protecting group and treating the resulting 5'-hydroxyl as described above or using a different nucleoside phosphoramidite (e.g., those known in the art). Alternatively, if the synthesis of the oligonucleotide chain is complete, the oligonucleotide may be subjected to further modifications (e.g., capping the 5' end). If the oligonucleotide chain is linked through a linker to solid support, the linker may be cleaved using methods known in the art after the synthesis of the oligonucleotide chain is complete. The remainder of the ring-opened chiral auxiliaries of the invention may be removed from phosphotriesters through hydrolysis with aqueous ammonia (30% (w/w)) (e.g., by heating for 12-24 hours at, e.g., about 55° C.). The remainder of the ring-opened chiral auxiliaries of the invention may be removed before, after, or concomitantly with the oligonucleotide chain removal from the solid support.

A non-limiting example of an oligonucleotide synthesis route is shown in Scheme 1.

Scheme 1

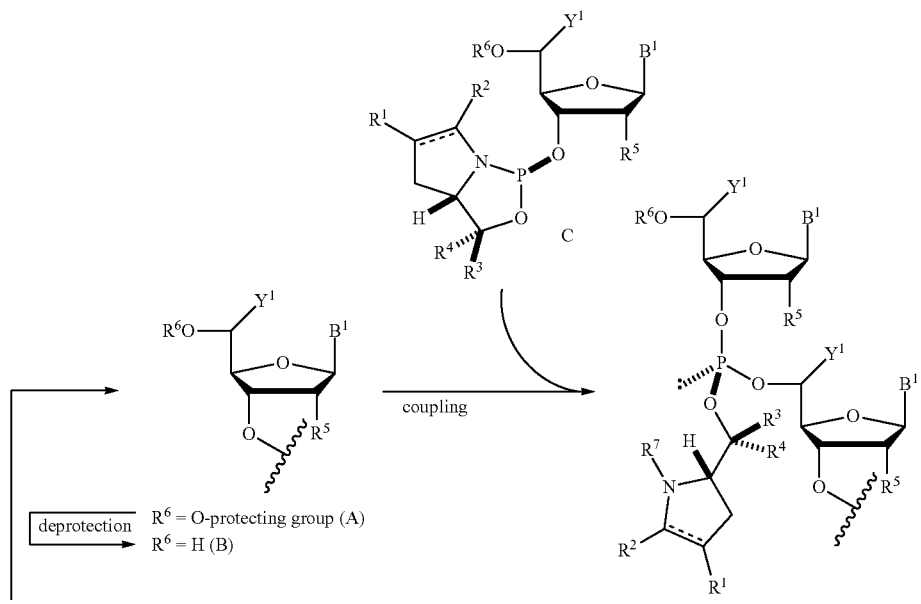

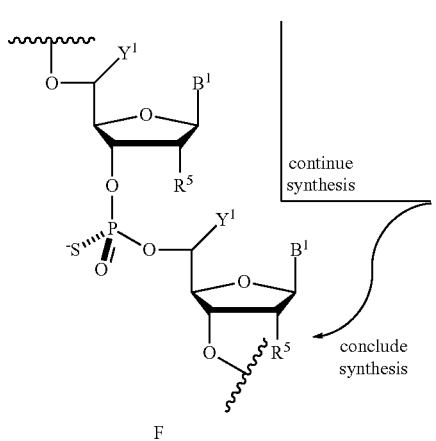

F

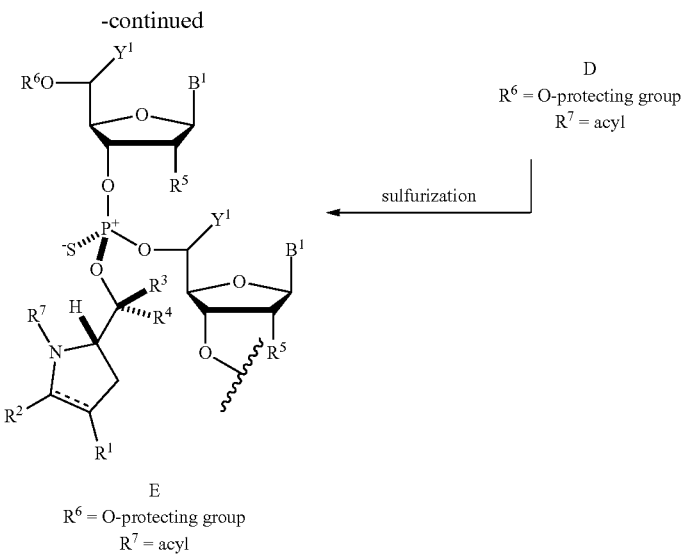

E
R⁶ = O-protecting group
R⁷ = acyl

As shown in Scheme 1, compound A, which is a protected nucleoside optionally linked to a solid support, may be subjected to a deprotection reaction to remove the 0-protecting group (e.g., DMT) at R⁶ and produce compound B. Compound B is then coupled to phosphoramidite C to produce phosphite D. In certain embodiments (e.g., when the nucleoside phosphoramidite includes 2'-deoxyribose, e.g., when R⁵ is H), the coupling activator is preferably CMPT.

Compound D is oxidized using a sulfurizing agent to afford phosphorothioate E with retention of stereochemistry.

Nucleoside phosphoramidites including phosphoramidites of formula (IA), (IB), (IC), and (ID) can be in the synthesis of oligonucleotides in accordance with the procedure described above using reaction conditions known in the art.

Preparation of Nucleoside Phosphoramidites
Phosphoramidite Precursors

The nucleoside phosphoramidites of the invention may be prepared from a compound of formula:

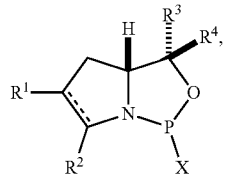
(VIIIA)

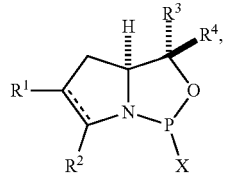
(VIIIB)

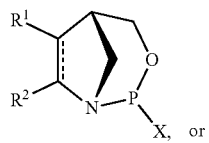
(VIIIC)

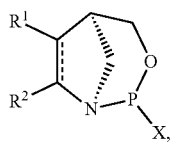
(VIIID)

where

=== is a single carbon-carbon bond or a double carbon-carbon bond;

X is a halogen (e.g., Cl or Br) or pseudohalogen;

each of R¹ and R² is independently an optionally substituted $C_{1-6}$ alkyl or optionally substituted $C_{6-10}$ aryl, or R¹ and R², together with the atoms to which each is attached, combine to form an optionally substituted 5- to 8-membered ring; and each of R³ and R⁴ is independently H, optionally substituted $C_{1-6}$ alkyl, or optionally substituted $C_{6-10}$ aryl.

In particular embodiments, the precursor to a nucleoside phosphoramidite may be a compound of formula:

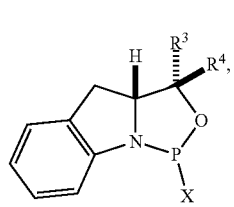
(IXA)

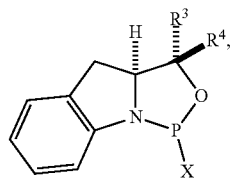
(IXB)

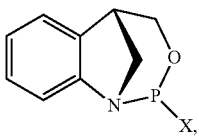
(IXC)

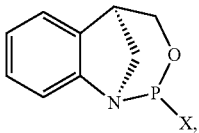
(IXD)

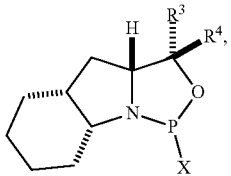
(IXA')

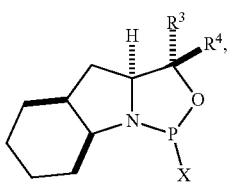
(IXB')

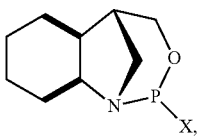
(IXC')

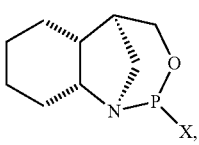
(IXD')

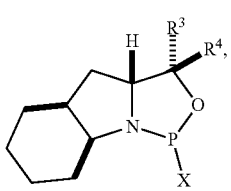
(IXA")

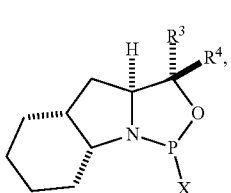
(IXB")

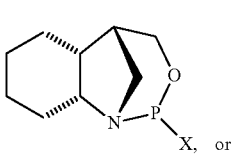
(IXC"), or

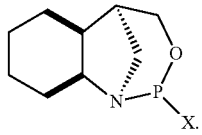
(IXD")

where
each of $R^3$ and $R^4$ is independently H, optionally substituted $C_{1-6}$ alkyl, or optionally substituted $C_{6-10}$ aryl; and X is halogen (e.g., Cl or Br) or pseudohalogen.

A non-limiting example of the preparation of a nucleoside phosphoramidite of the invention is shown in Scheme 2.

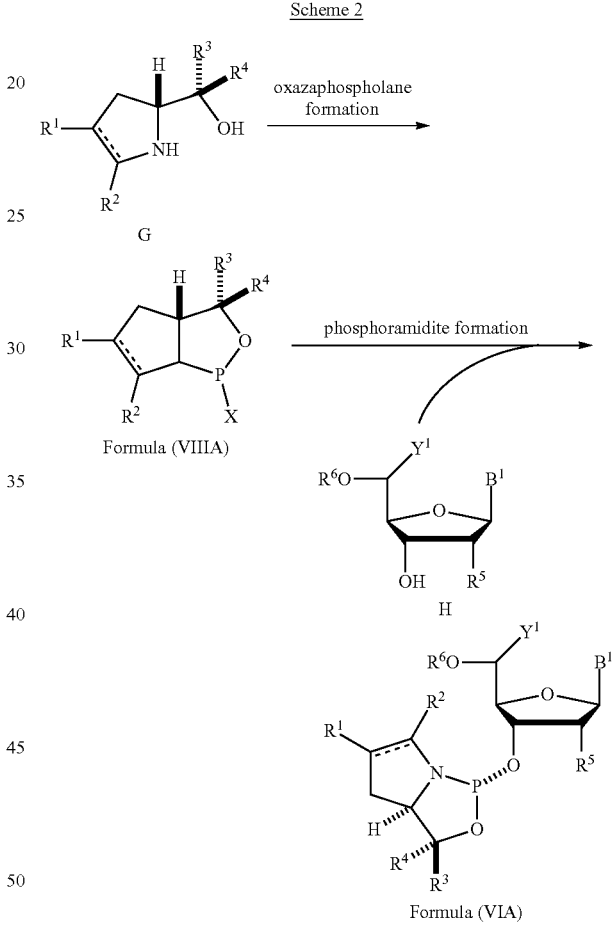

Scheme 2

As shown in Scheme 2, aminoalcohol G can be converted to oxazaphospholane of formula (VIIIA) using an electrophilic source of phosphorus (III), e.g., phosphorus (III) halide (e.g., PCl₃). An oxazaphospholane of formula (VIIIA) may be coupled to nucleoside H to give a nucleoside phosphoramidite of formula (VIA). The reaction conditions useful for this coupling are known in the art and typically involve the use of a sterically hindered organic base (e.g., N,N-diisopropylethylamine). Typically, the oxazaphospholane formation and phosphoramidite formation are performed in a one-pot transformation without isolation or purification of the oxazaphospholane of formula (VIIIA).

Nucleoside phosphoramidites including phosphoramidites of formula (VA), (VB), (VC), and (VD) can be prepared according to the procedure described above using reaction conditions known in the art.

Aminoalcohol G and its enantiomer can be prepared from the corresponding amino acid using methods and reactions known in the art. Aminoalcohol G can be used in the preparation of compounds containing a P-stereogenic group of formula (IA) or (IB) (e.g., compounds of formula (IIIA) or (IIIB)). Aminoalcohol I and its enantiomer for the preparation of phosphoramidites of formula (VC) and (VD) can be prepared from the corresponding amino acids using methods and reactions known in the art. Aminoalcohol I can be used in the preparation of compounds containing a P-stereogenic group of formula (IC) or (ID) (e.g., compounds of formula (IIIC) or (IIID)). Aminoalcohol I is a compound of the following structure:

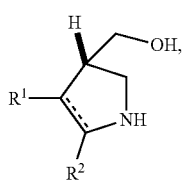

where each of $R^1$ and $R^2$ is independently optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring.

Advantageously, when $R^3$ and $R^4$ are each H, nucleoside phosphoramidites of the invention can be prepared through a short reaction sequence of only three steps, two of which can be carried out in one pot.

The following examples are meant to illustrate the invention. They are not meant to limit the invention in any way.

EXAMPLES

Chiral Auxiliaries and Phosphoramidites

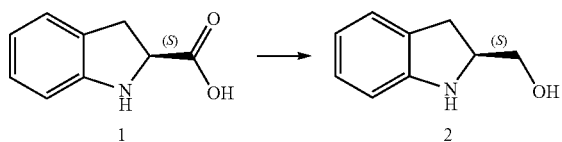

To a solution of (2S)-dihydro-1H-indole-2-carboxylic acid 1 (1.63 g, 10.0 mmol) in ether (50 mL) was added a solution of LiAlH$_4$ in THF (2M, 7.5 mL, 15.0 mmol) under argon, and the mixture was stirred overnight. After completion of the reaction, the mixture was quenched with Na$_2$SO$_4$·10H$_2$O. The solid was filtered off and washed with ethyl acetate, and the filtrate was dried over anhydrous Na$_2$SO$_4$. The mixture was filtered, and the solvent evaporated to give a residue, which was subjected to flash silica gel column purification on an ISCO (hexane/ethyl acetate, 10-70%) to give 1.44 g (96%) of compound 2 as a gray solid. $^1$H NMR (500 MHz, CDCl$_3$; ppm): δ7.10 (1H, d, J 7.5 Hz), 7.04 (1H, t, J 7.5 Hz), 6.75 (1H, t, J 7.5 Hz), 6.69 (1H, d, J 7.5 Hz), 4.10-4.06 (2H, m), 3.75 (1H, dd, J 11.0, 4.0 Hz), 3.60 (1H, dd, J 11.0, 6.0 Hz), 3.12 (1H, dd, J 16.0, 9.0 Hz), 2.87 (1H, dd, J 16.0, 8.0 Hz); ESI MS for C$_9$H$_{11}$NO calculated 149.2, observed [M+H]$^+$ 150.1.

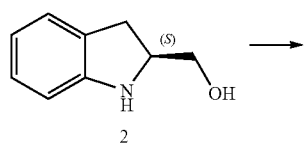

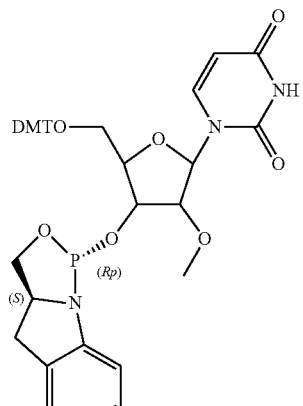

To a solution of compound 2 (1.0 g, 6.7 mmol) in anhydrous THF (5 mL) was added N,N-diisopropylethylamine (2.41 mL, 13.4 mmol) under argon. The resulting mixture was added dropwise to a solution of phosphorus trichloride (0.58 mL, 6.7 mmol) in anhydrous THF (8 mL) at 0° C. under argon. The mixture was warmed to room temp and stirred for 1.5 h. In a separate round bottom flask, a solution of 5'-O-(4,4'-dimethoxytrityl)-2'-methoxy-uridine (2.25 g, 4.0 mmol) and N,N-diisopropylethylamine (4.81 mL, 26.8 mmol) in THF (5 mL) under argon was cooled to −78° C., and the above mixture was slowly added. The mixture was warmed to room temp, stirred for 3 h, diluted with dichloromethane (30 mL), and washed with saturated aqueous sodium bicarbonate (20 mL). The organic layer dried over anhydrous sodium sulfate and filtered. The filtrate was evaporated to afford a residue, which was subjected to flash silica gel amine column purification on an ISCO (1-8% methanol in dichloromethane) to give 1.14 g (39%) of the title compound 3 as a white foam. ESI MS for C$_{40}$H$_{40}$N$_3$O$_9$P Calculated 737.7, Observed 738.2 (M+1); $^{31}$P NMR (202 MHz, CDCl$_3$): δ141.2 (s).

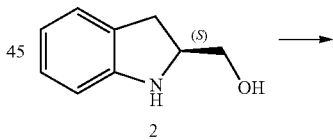

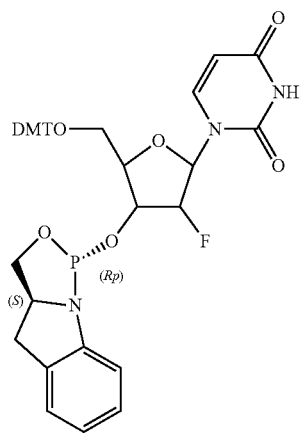

Compound 4 was prepared by the same procedure as reported here for Compound 3 using 5'-O-(4,4'-dimethoxytrityl)-2'-fluoro-uridine as a starting material. Compound 4 was produced in 24% yield. ESI MS for C$_{39}$H$_{37}$FN$_3$O$_8$P Calculated 725.7, Observed 748.3 (M+Na); $^{31}$P NMR (202 MHz, CDCl$_3$): δ141.0 (s).

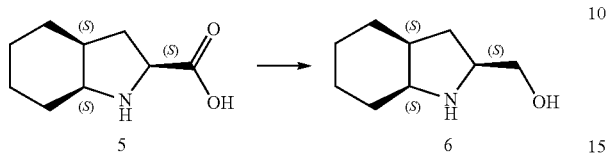

To a solution of (2S,3aS,7aS)-octahydro-1H-indole-2-carboxylic acid 5 (1.69 g, 10.0 mmol) in ether (50 mL) was added a solution of LiAlH$_4$ in THF (2M, 7.5 mL, 15 mmol) under argon, and the mixture was stirred overnight. After completion of the reaction, the mixture was quenched with Na$_2$SO$_4$·10H$_2$O, and the solids were filtered off and washed with ethyl acetate. The filtrate was dried over anhydrous Na$_2$SO$_4$ and evaporated to give 1.23 g (79%) of the crude compound 6 as a colorless oil. $^1$H NMR (500 MHz, CDCl$_3$; ppm): δ3.70 (1H, dd, J 11.0, 3.5 Hz), 3.60 (1H, dd, J 11.0, 6.0 Hz), 3.50-3.40 (1H, m), 3.24 (1H, q, J 6.0 Hz), 2.13-2.08 (1H, m), 1.94-1.86 (1H, m), 1.75-1.65 (1H, m), 1.65-1.40 (6H, m), 1.35-1.23 (2H, m); ESI MS for C$_9$H$_{11}$NO calculated 155.2, observed [M+H]$^+$ 156.1.

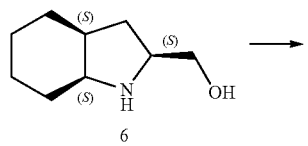

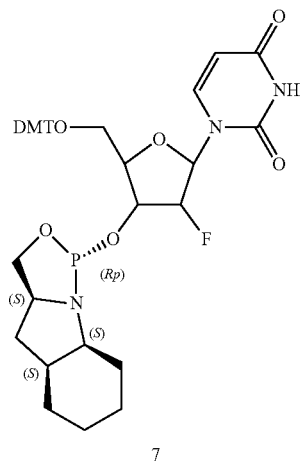

Compound 7 was prepared by the same procedure as reported here for Compound 3 using 5'-O-(4,4'-dimethoxytrityl)-2'-fluoro-uridine as a starting material. ESI MS for C$_{39}$H$_{43}$FN$_3$O$_8$P calculated 731.7, observed 732.2 (M+1); $^{31}$P NMR (202 MHz, CDCl$_3$): δ140.7 (s).

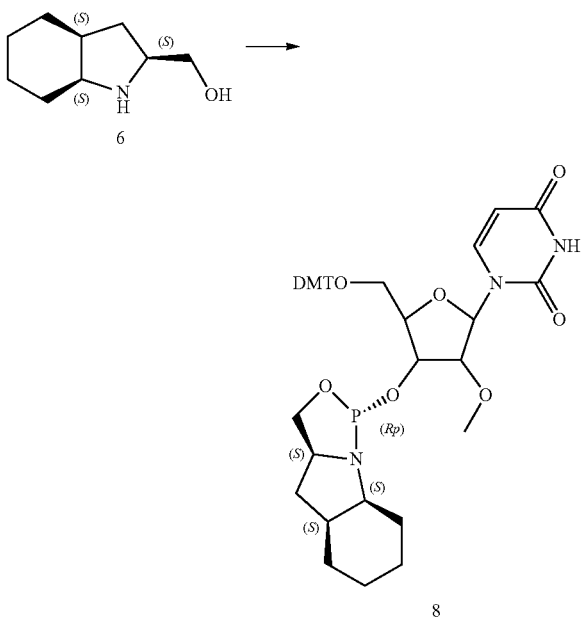

Compound 8 was prepared by the same procedure as reported here for Compound 3 using 5'-O-(4,4'-dimethoxytrityl)-2'-methoxy-uridine as a starting material. ESI MS for C$_{40}$H$_{46}$N$_3$O$_9$P calculated 743.8, observed 742.5 (M−1); $^{31}$P NMR (202 MHz, CDCl$_3$): δ140.0 (s).

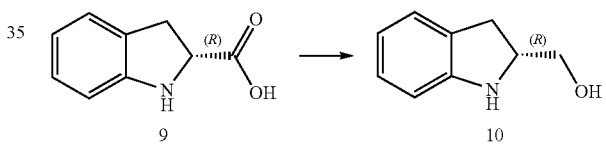

To a solution of (2R)-dihydro-1H-indole-2-carboxylic acid 9 (4.90 g, 30.0 mmol) in ether (100 mL) was added a solution of LiAlH$_4$ in THF (2M, 22.5 mL, 45 mmol) under argon, and the mixture was stirred overnight. After completion of the reaction, the reaction mixture was quenched with Na$_2$SO$_4$·10H$_2$O, and the solids were filtered off and washed with ethyl acetate. The filtrate was dried over anhydrous Na$_2$SO$_4$, the mixture was filtered, and the solvent evaporated to give a residue, which was subjected to flash silica gel column purification on an ISCO (hexane/ethyl acetate, 10-70%) to give 3.68 g (82%) of compound 10 as a gray solid. $^1$H NMR (500 MHz, CDCl$_3$; ppm): δ7.10 (1H, d, J 7.5 Hz), 7.04 (1H, t, J 7.5 Hz), 6.75 (1H, t, J 7.5 Hz), 6.69 (1H, d, J 7.5 Hz), 4.10-4.06 (1H, m), 3.75 (1H, dd, J 11.0, 4.0 Hz), 3.60 (1H, dd, J 11.0, 6.0 Hz), 3.12 (1H, dd, J 16.0, 9.0 Hz), 2.87 (1H, dd, J 16.0, 8.0 Hz); ESI MS for C$_9$H$_{11}$NO calculated 149.2, observed [M+H]$^+$ 150.1.

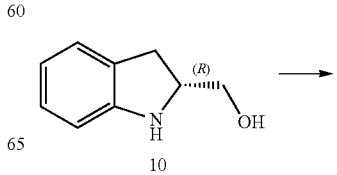

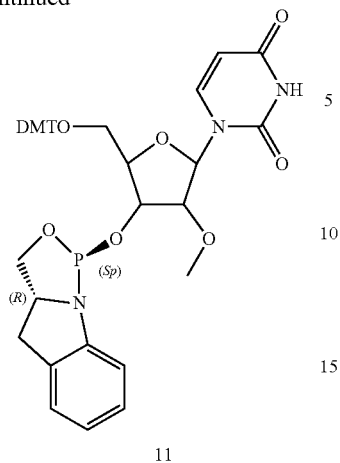

11

Compound 11 was prepared by the same procedure as reported here for Compound 3 using 5'-O-(4,4'-dimethoxytrityl)-2'-methoxy-uridine as a starting material. Compound 11 was produced in 56% yield. ESI MS for $C_{40}H_{40}N_3O_9P$ calculated 737.7, observed 738.2 (M+1); $^{31}$P NMR (202 MHz, CDCl$_3$): δ141.3 (s).

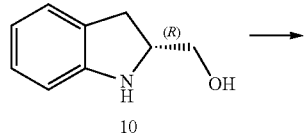

10

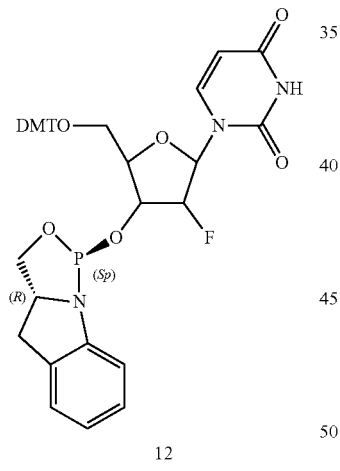

12

Compound 12 was prepared by the same procedure as reported here for Compound 3 using 5'-O-(4,4'-dimethoxytrityl)-2'-fluoro-uridine as a starting material. Compound 12 was produced in 72% yield. ESI MS for $C_{39}H_{37}FN_3O_8P$ Calculated 725.7, Observed 748.3 (M+Na); $^{31}$P NMR (202 MHz, CDCl$_3$): δ141.8 (s).

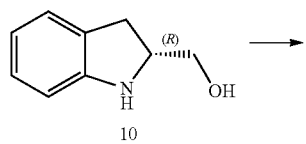

10

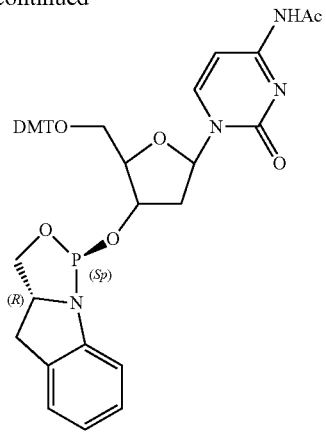

13

Compound 13 was prepared by the same procedure as reported here for Compound 3 using 5'-O-(4,4'-dimethoxytrityl)-2'-deoxy-cytidine (N-acetyl) as a starting material. Compound 13 was produced in 33% yield. ESI MS for $C_{41}H_{41}N_4O_8P$ Calculated 748.8, Observed 747.4 (M-1); $^{31}$P NMR (202 MHz, CDCl$_3$): δ140.2 (s).

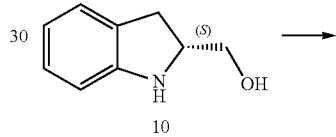

10

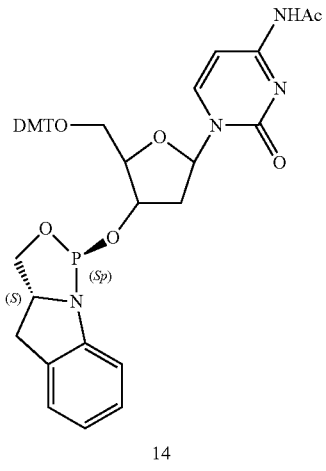

14

Compound 14 was prepared by the same procedure as reported here for Compound 3 using 5'-O-(4,4'-dimethoxytrityl)-2'-deoxy-cytosine (N-acetyl) as a starting material. Compound 14 was produced in 27% yield. ESI MS for $C_{41}H_{41}N_4O_8P$ Calculated 748.8, Observed 747.4 (M-1); $^{31}$P NMR (202 MHz, CDCl$_3$): δ139.7 (s).

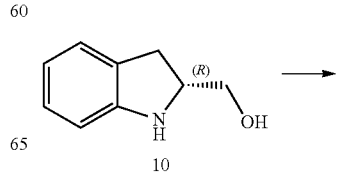

10

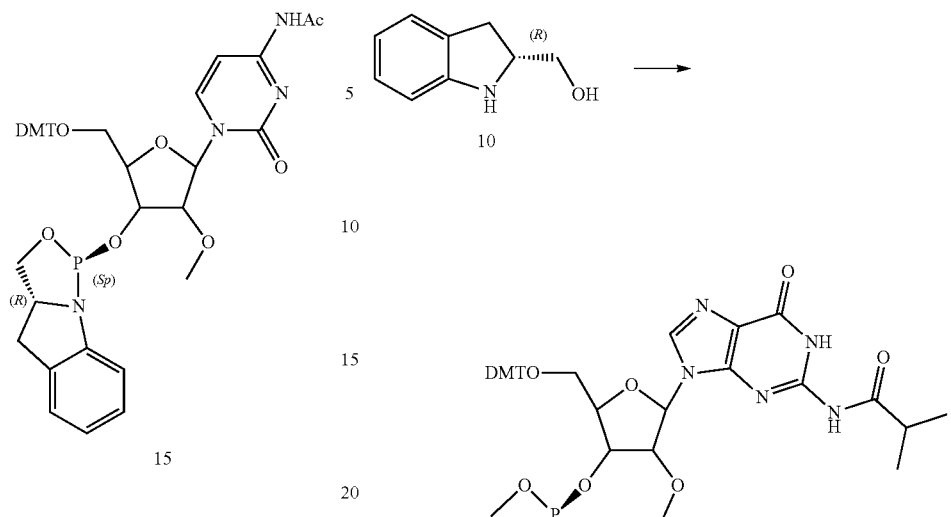

Compound 15 was prepared by the same procedure as reported here for Compound 3 using 5'-O-(4,4'-dimethoxytrityl)-2'-methoxy-cytosine (N-acetyl) as a starting material. Compound 15 was produced in 35% yield. ESI MS for $C_{42}H_{43}N_4O_8P$ Calculated 778.8, Observed 779.3 (M); $^{31}P$ NMR (202 MHz, $CDCl_3$): δ141.0(s).

Compound 16 was prepared by the same procedure as reported here for Compound 3 using 5'-O-(4,4'-dimethoxytrityl)-2'-methoxy-adenosine (N-benzoyl) as a starting material. Compound 16 was produced in 48% yield. ESI MS for $C_{48}H_{45}N_6O_8P$ Calculated 864.8, Observed 865.3 (M); $^{31}P$ NMR (202 MHz, $CDCl_3$): δ140.0 (s).

Compound 17 was prepared by the same procedure as reported here for compound 3 using 5'-O-(4,4'-dimethoxytrityl)-2'-methoxy-guanosine (N-i-butyryl) as a starting material. Compound 17 was produced in 10% yield. ESI MS for $C_{45}H_{47}N_6O_9P$ Calculated 846.9, Observed 847.3 (M); $^{31}P$ NMR (202 MHz, $CDCl_3$): δ138.9 (s).

Compounds listed in Table 1 were prepared by the same procedure as reported here for compound 3.

TABLE 1

| Compound | Chemical Yield (%) | $^{31}P$ NMR (202 MHz) |
| --- | --- | --- |
|  | 33 | — |

TABLE 1-continued
| Compound | Chemical Yield (%) | 31P NMR (202 MHz) |
|---|---|---|
| 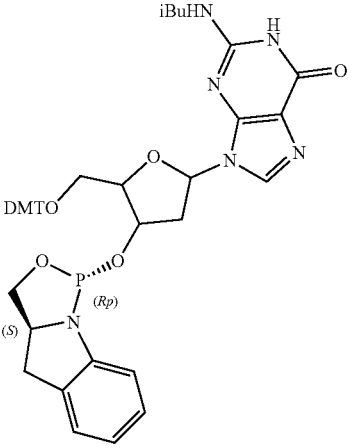 | 26 | — |
| 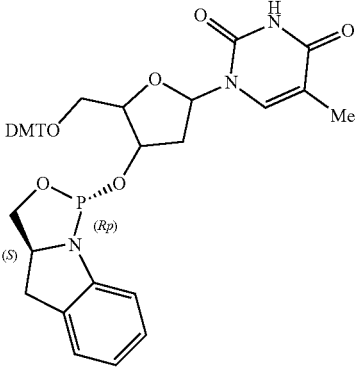 | 34 | δ138.84 (s) |
| 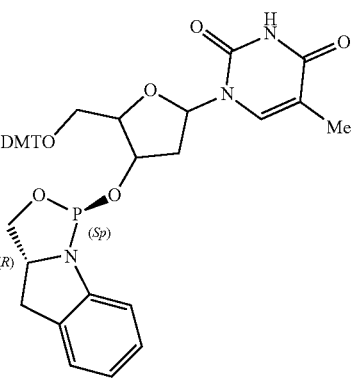 | 33 | δ138.53 (s) |
TABLE 1-continued
| Compound | Chemical Yield (%) | 31P NMR (202 MHz) |
|---|---|---|
| 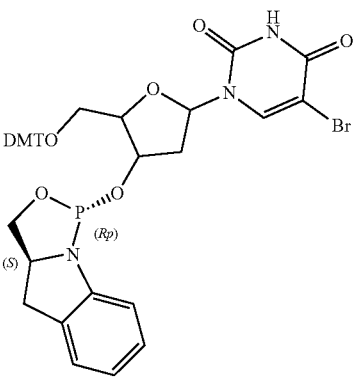 | 57 | δ138.90 (s) |
| 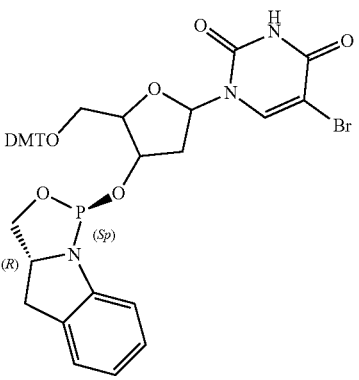 | 44 | δ139.58 (s) |
| 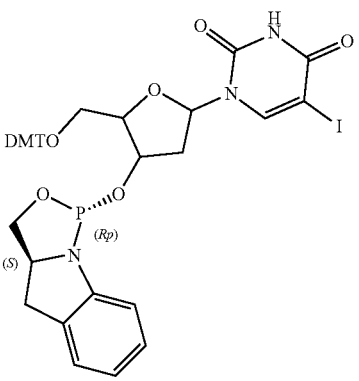 | 45 | δ138.63 (s) |
| 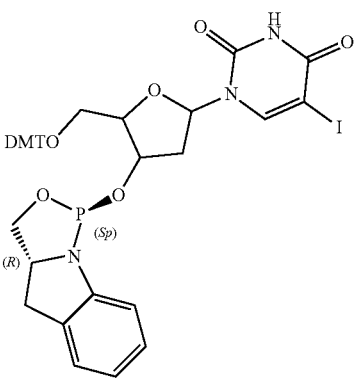 | 42 | δ139.41 (s) |

TABLE 1-continued

| Compound | Chemical Yield (%) | $^{31}$P NMR (202 MHz) |
|---|---|---|
| (structure: DMTO-sugar with NHAc-cytosine base, OMe, and (Rp) phosphoramidite with (S)-indoline) | 32 | δ140.93 (s) |
| (structure: DMTO-sugar with iBuHN-guanine base, OMe, and (Rp) phosphoramidite with (S)-indoline) | 14 | δ139.13 (s) |

*iBu in this table stands for isobutyryl.

Synthesis of the Polynucleotide Constructs

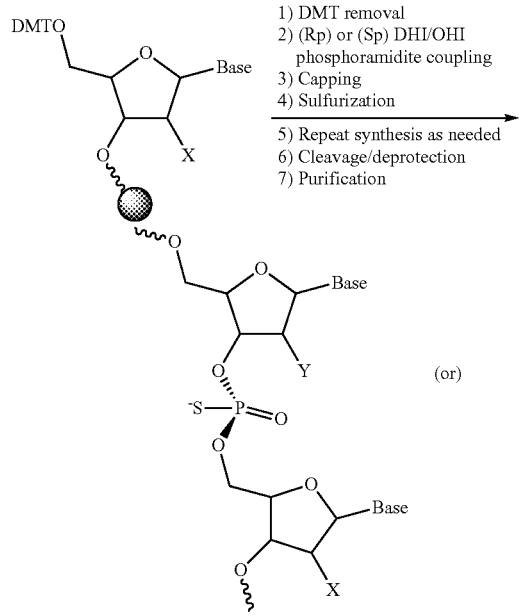
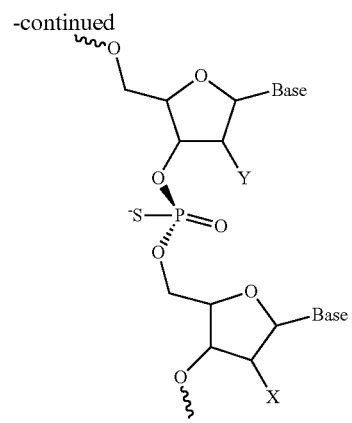

1) DMT removal
2) (Rp) or (Sp) DHI/OHI phosphoramidite coupling
3) Capping
4) Sulfurization
5) Repeat synthesis as needed
6) Cleavage/deprotection
7) Purification All the polynucleotide constructs synthesized were modified at the 2'-ribose sugar position with 2'-F, 2'-OMe, or 2'-deoxy modification. 0-protecting groups, such as 2'-OTBDMS, can also be used. Automated polynucleotide synthesis (1 μmol scale) was carried out with the following reagents/solvents:

Solid support—CPG Glen Uny support
Coupling agent—0.25 M BTT in acetonitrile
Oxidizer—0.02 M I2 in THF/Pyridine/H$_2$O (2×30 s oxidation per cycle)
Deblock—3% Trichloroacetic Acid/DCM (2×40 s deblocks per cycle)
Cap Mix A—THF/2, 6-Lutidine/Ac$_2$O (2×30 s capping per cycle)
Cap Mix B—16% Methyl imidazole in THF (2×30 s capping per cycle)
Sulfurization—0.05 M sulfurizing reagent, 3-((N,N-dimethylaminomethylidene)amino)-3H-1,2,4-dithiazole-5-thione (DDTT), in 60% pyridine/40% acetonitrile (3×60 s sulfurization per cycle)
Coupling—Phosphoramidites were suspended to a concentration of 100 mM in anhydrous acetonitrile prior to synthesis, phosphoramidite activation was performed with 2.5-fold molar excess of BTT, 0.25 M in acetonitrile. Activated phosphoramidites were coupled for 3×60 seconds per cycle Polynucleotide Deprotection and Purification Protocol:
When polynucleotides contain standard nucleobase protecting groups (such as A-Bz, C-Ac and G-iBu etc.), the following cleavage and deprotection conditions were used:
polynucleotides were cleaved and deprotected in 1.0 mL of AMA (1:1 ratio of 36% aq. ammonia and 40% methylamine in methanol) for 2 h at room temperature followed by centrifugal evaporation.
Crude polynucleotide pellets were re-suspended in 100 μL of 50% acetonitrile/water, briefly heated to 65° C., and vortexed thoroughly. Total 100 μL crude polynucleotide samples were injected onto reverse phase HPLC with the following buffers/gradient:
Buffer A=50 mM aqueous triethylammonium acetate (TEAA)
Buffer B=90% acetonitrile in water
Flow Rate=1 mL/min
Gradient:
0-2 min (100% Buffer A/0% Buffer B)
2-42 min (0% to 60% Buffer B)
42-55 min (60% to 100% Buffer B)

Across the dominant reverse phase HPLC peaks, 0.5 mL fractions were collected and analyzed by MALDI-TOF mass spectrometry to confirm the presence of compounds with the desired mass peaks. Purified fractions containing compounds with the correct mass peaks were frozen and lyophilized. Once dry, fractions were re-suspended, combined with corresponding fractions, frozen, and lyophilized to give the final product.

Polynucleotides requiring additional deprotection were initially isolated as described above followed by the necessary secondary deprotection steps (see below):

Secondary Deprotection of Polynucleotides Having TBDMS Protection:

Reverse phase HPLC-purified polynucleotide products were re-suspended in 219 μL of anhydrous DMSO, heated briefly to 65° C., and vortexed thoroughly. To the DMSO solution, 31 μL of 6.1 M triethylamine trihydrofluoride (TEA.3HF) was added to give a final concentration of 0.75 M. The reaction was allowed to proceed at room temperature for ~1 h per TBDMS-protected hydroxyl modification. Reaction was monitored by MALDI-TOF mass spectrometry to confirm complete deprotection. Once deprotection was complete, 35 μL of 3M sodium acetate and 1 mL of butanol were sequentially added. Samples were vortexed thoroughly and placed at −80° C. for 2 h. After 2 h, samples were centrifuged to pellet the polynucleotides. The butanol layer was removed, and the polynucleotide pellet was re-suspended in 1 mL of aqueous 20% acetonitrile. Samples were gel-filtered for isolation of the final polynucleotide construct.

Synthesis of Polynucleotide Constructs with Stereochemically Enriched Internucleoside Phosphorothioates (PS):

The following modified experimental conditions have been used for the synthesis of polynucleotide constructs including stereochemically enriched internucleoside phosphorothioates from chiral phosphoramidite monomers. Automated polynucleotide synthesis (1 μmol scale) was carried out with the following reagents/solvents:

Solid support—CPG Glen Uny support
Coupling agent—BTT/ETT/CMPT/phenyl imidazole as required
Oxidizer—0.02 M $I_2$ in THF/Pyridine/$H_2O$ (2×30 s oxidation per cycle)
Deblock—3% dichloroacetic Acid/DCM (2×40 s deblocks per cycle)
Cap Mix A—THF/2,6-lutidine/$Ac_2O$ (2×30 s capping per cycle)
Cap Mix B—16% methyl imidazole in THF (2×30 s capping per cycle)
Sulfurization—0.05 M sulfurizing reagent, 3-((N,N-dimethylaminomethylidene)amino)-3H-1,2,4-dithiazole-5-thione (DDTT), in 60% pyridine/40% acetonitrile (3×120 s sulfurization per cycle)
Coupling—chiral phosphoramidites (e.g., compounds of formula (IIA) or (IIB)) were suspended to a concentration of 100 mM in anhydrous acetonitrile prior to synthesis, phosphoramidite activation was performed with 2.5-fold molar excess of respective activators as specified (BTT=0.25 M in acetonitrile, CMPT=0.5 M in acetonitrile, Ph-Imidazole=0.5 M in Acetonitrile). Activated chiral phosphoramidites were coupled for 3×200 seconds per cycle.

Chiral Polynucleotide Deprotection and Purification Protocol:

Following automated polynucleotide synthesis, stereopure phosphorothioate containing polynucleotides with standard nucleobase protecting groups (such as A-Bz, C-Ac, and G-iBu etc.) and chiral auxiliary were deprotected and cleaved with the following conditions: DMT protected chiral phosphorothioate polynucleotides on solid support was suspended in 1.0 mL of aqueous ammonia (30 wt %) and heated at 55° C. for 12-24 h, followed by centrifugal evaporation.

Crude chiral polynucleotide pellets were re-suspended in 100 μL of 50% acetonitrile, briefly heated to 65° C., and vortexed thoroughly. Total 100 μL crude polynucleotide samples were injected onto reverse phase HPLC with the following buffers/gradient:

Buffer A=100 mM aqueous triethylammonium acetate (TEAA)
Buffer B=90% acetonitrile in water
Flow Rate=1 mL/min
Gradient:
  0-2 min (100% Buffer A/0% Buffer B)
  2-50 min (0% to 45% Buffer B)
  50-55 min (45% to 100% Buffer B)

Across the dominant reverse phase HPLC peaks, 1.0 mL fractions were collected and analyzed by MALDI-TOF mass spectrometry to confirm the presence of compounds with the desired mass peaks. Purified fractions containing compounds with the correct mass peaks were frozen and lyophilized. Once dry, fractions were re-suspended, combined with corresponding fractions, frozen, and lyophilized to give the final product.

Analysis of Stereochemical Purity of Phosphorothioate Containing Polynucleotides:

DMT protected oligonucleotides with stereochemically enriched phosphorothioates were analyzed by HPLC/UPLC to determine the diastereoselectivity of $R_P$ and $S_P$ isomers. The absolute stereochemical identity of the internucleoside phosphorothioate identified with an asterisk (*) was determined through comparison of the HPLC traces of the oligonucleotides of the invention to the HPLC traces of authentic racemic and diastereomerically enriched oligonucleotides that were prepared using methods known in the art. The HPLC conditions were as follows:

Reverse Phase HPLC
Column: AdvancedBio Oligonucleotide, 2.1×100 mm, 2.7 μm
Mobile Phase A: 100 mM tetraethylammonium acetate in water
Mobile Phase B: acetonitrile
Gradient: 10-12% mobile phase B in 45 min
Column Temperature: 60° C.
Flow Rate: 0.35 mL/min
Detection: 260 nm (UV)

For comparison, reference standards of the same oligonucleotide with $R_P$ and $S_P$ isomers were prepared using literature methods as described elsewhere (Oka et al., Chem. Soc. Rev., 40:5829-5843, 2011; Oka et al., Org. Lett., 11:967-970, 2009; and U.S. pre-grant publication Nos. 2013/0184450 and 2015/0197540).

Diastereomer ratios ($S_P$:$R_P$) have been established by integrating the product peaks in UPLC traces of the prepared oligonucleotides. Absolute stereochemical identity of the dominant diastereomer was determined by comparison to the reference standard. UPLC was performed as follows. Samples were dissolved in water, injected onto UPLC, and analyzed under the following conditions:

Column: Xbridge C18, 4.6×150 mm, 5 μm
Mobile phase A=50 mM aqueous triethylammonium acetate (TEAA) in water
Mobile phase B=Acetonitrile in water
Flow Rate=1 mL/min
Column Temperature=50° C.
Detection=260 nm
Gradient:
  0-1 min (90% mobile phase A/10% mobile phase B)
  1-30 min (88.5% mobile phase A/11.5% mobile phase B)

The stereochemical purity, stereochemical identity, and coupling activators used in the synthesis of the prepared oligonucleotides are shown in Table 2.

TABLE 2

| Entry | Oligonucleotide (5'-3') | Activator | PN | (**) | Sp:Rp |
|---|---|---|---|---|---|
| 1 | uUGAAGUAAA | BTT | Racemic | Racemic | Racemic |
| 2 | u*UGAAGUAAA | BTT | $(R_P)$-OHI | $(S_P)$ | >99.0:<1.0 |
| 3 | u*UGAAGUAAA | BTT | $(R_P)$-DHI | $(S_P)$ | >99.0:<1.0 |
| 4 | u*UGAAGUAAA | PhIMT | $(R_P)$-OHI | $(S_P)$ | >99.0:<1.0 |
| 5 | u*UGAAGUAAA | PhIMT | $(R_P)$-DHI | $(S_P)$ | >99.0:<1.0 |
| 6 | u*UGAAGUAAA | CMPT | $(R_P)$-OHI | $(S_P)$ | >99.0:<1.0 |
| 7 | u*UGAAGUAAA | CMPT | $(R_P)$-DHI | $(S_P)$ | >99.0:<1.0 |
| 8 | uUGAAGUAAA | BTT | Racemic | Racemic | Racemic |
| 9 | u*UGAAGUAAA | BTT | $(R_P)$-OHI | $(S_P)$ | 91:11 |
| 10 | u*UGAAGUAAA | BTT | $(R_P)$-DHI | $(S_P)$ | >99.0:<1.0 |
| 11 | u*UGAAGUAAA | CMPT | $(R_P)$-OHI | $(S_P)$ | 95.0:5.0 |
| 12 | u*UGAAGUAAA | CMPT | $(R_P)$-DHI | $(S_P)$ | >99.0:<1.0 |
| 13 | u*UGAAGUAAA | PhIMT | $(R_P)$-OHI | $(S_P)$ | >99.0:<1.0 |
| 14 | u*UGAAGUAAA | PhIMT | $(R_P)$-DHI | $(S_P)$ | >99.0:<1.0 |
| 15 | u*UGAAGUAAA | BTT | $(S_P)$-DHI | $(R_P)$ | 18:82 |
| 16 | u*UGAAGUAAA | BTT | $(S_P)$-DHI | $(R_P)$ | <1:>99.0 |
| 17 | u*UGAAGUAAA | CMPT | $(S_P)$-DHI | $(R_P)$ | 1.7:98.3 |
| 18 | u*UGAAGUAAA | CMPT | $(S_P)$-DHI | $(R_P)$ | <1:>99.0 |
| 19 | u*UGAAGUAAA | PhIMT | $(S_P)$-DHI | $(R_P)$ | 4.2:95.8 |
| 20 | u*UGAAGUAAA | PhIMT | $(S_P)$-DHI | $(R_P)$ | 7.4:92.6 |
| 21 | mNUAAGUAAA | BTT | Racemic | Racemic | Racemic |
| 22 | m*NUAAGUAAA | BTT | $(S_P)$-DHI | $(R_P)$ | 16:84 |
| 23 | m*NUAAGUAAA | BTT | $(R_P)$-DHI | $(S_P)$ | 73.9:26.1 |
| 24 | m*NUAAGUAAA | CMPT | $(S_P)$-DHI | $(R_P)$ | <1.0:>99.0 |
| 25 | m*NUAAGUAAA | CMPT | $(R_P)$-DHI | $(S_P)$ | 96.3:3.7 |
| 26 | m*NUAAGUAAA | PhIMT | $(S_P)$-DHI | $(R_P)$ | 12.1:87.9 |
| 27 | m*NUAAGUAAA | PhIMT | $(R_P)$-DHI | $(S_P)$ | 74.4:25.6 |
| 28 | aUGAAGUAAA | BTT | Racemic | Racemic | Racemic |
| 29 | a*UGAAGUAAA | CMPT | $(S_P)$-DHI | $(R_P)$ | <1.0:>99.0 |
| 30 | mUGAAGUAAA | BTT | Racemic | Racemic | Racemic |
| 31 | m*UGAAGUAAA | CMPT | $(S_P)$-DHI | $(R_P)$ | <1.0:>99.0 |
| 30 | gUGAAGUAAA | BTT | Racemic | Racemic | Racemic |
| 31 | g*UGAAGUAAA | CMPT | $(S_P)$-DHI | $(R_P)$ | <1.0:>99.0 |
| 32 | aNUAAGUAAA | BTT | Racemic | Racemic | Racemic |
| 33 | a*NUAAGUAAA | CMPT | $(R_P)$-DHI | $(S_P)$ | 98.4:1.6 |
| 34 | gNUAAGUAAA | BTT | Racemic | Racemic | Racemic |
| 35 | g*NUAAGUAAA | CMPT | $(R_P)$-DHI | $(S_P)$ | 90.9:9.1 |
| 36 | tNUAAGUAAA | BTT | Racemic | Racemic | Racemic |
| 37 | t*NUAAGUAAA | CMPT | $(R_P)$-DHI | $(S_P)$ | 86.8:13.2 |

In Table 2, lower case u is uridine having 2'-F and a 3' position bonded to phosphorothioate; lower case bold u is uridine having 2'-OMe and a 3' position bonded to phosphorothioate; lower case a is 2'-deoxyadenosine having a 3' position bonded to phosphorothioate; lower case bold a is adenosine having a 2'-OMe and a 3' position bonded to phosphorothioate; lower case g is 2'-deoxyguanosine having a 3' position bonded to phosphorothioate; lower case bold g is guanosine having 2'-OMe and a 3' position bonded to phosphorothioate; lower case m is 2'-deoxycytidine having a 3' position bonded to phosphorothioate; lower case bold m is cytidine having 2'-OMe and a 3' position bonded to phosphorothioate; lower case t is 2'-deoxythymidine having a 3' position bonded to phosphorothioate; * indicates a stereochemically enriched internucleoside phosphorothioate; UPPER CASE LETTERS identify nucleosides having 2'-F and a 3' position bonded to phosphate; UPPER CASE BOLD LETTERS identify nucleosides having 2'-OMe and a 3' position bonded to phosphate; N is a 2'-deoxyguanosine having a 3' position bonded to phosphate; PN means phosphoramidite; (**) provides stereochemical identity of the internucleoside phosphorothioate identified with * in the oligonucleotide column; and DHI and OHI represent the following structures:

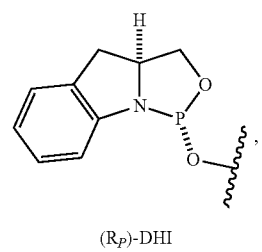

$(R_P)$-DHI

-continued

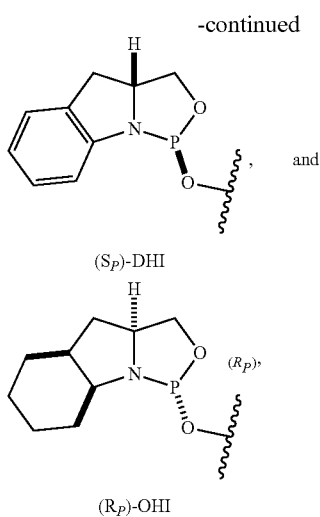

($S_P$)-DHI ($R_P$)-OHI respectively.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A compound of formula (IIIA) or (IIIB):

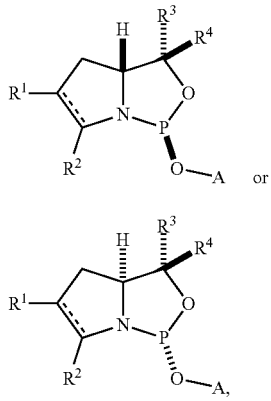

wherein

═══ is a single carbon-carbon bond or a double carbon-carbon bond;

A is an optionally substituted $C_{1-12}$ alkyl, optionally substituted $C_{3-10}$ cycloalkyl, optionally substituted $C_{3-10}$ cycloalkyl-$C_{1-6}$-alkyl, optionally substituted $C_{1-9}$ heterocyclyl, optionally substituted $C_{1-9}$ heterocyclyl-$C_{1-6}$-alkyl, sugar analogue, nucleoside, nucleotide, or oligonucleotide;

each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and each of $R^3$ and $R^4$ is independently H, optionally substituted $C_{1-6}$ alkyl, or optionally substituted $C_{6-10}$ aryl.

2. The compound of claim 1, wherein $R^1$ and $R^2$, together with the atoms to which each is attached, combine to form an optionally substituted 5- to 8-membered ring.

3. The compound of claim 1, wherein the compound is of the following structure:

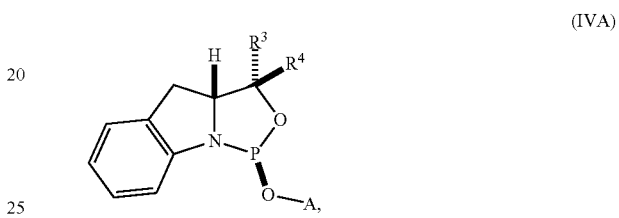

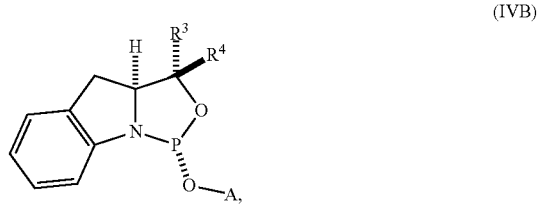

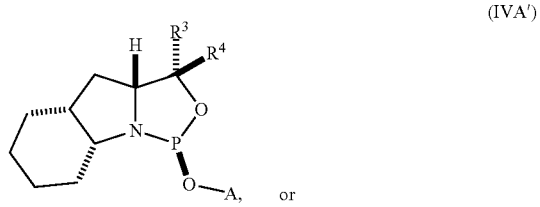

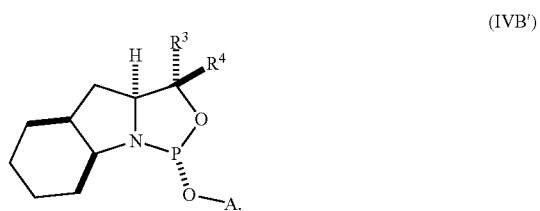

4. A nucleoside phosphoramidite comprising a sugar bonded to a nucleobase and to a phosphoramidite of the following structure:

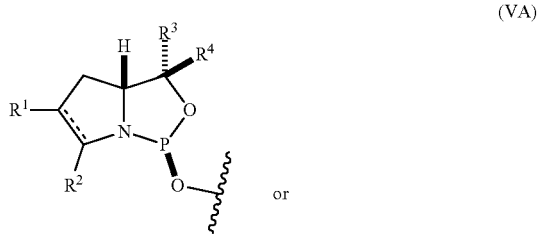

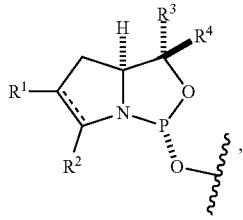
(VB)

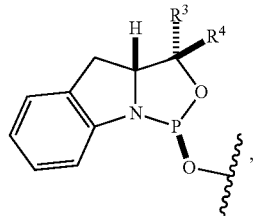
(VIIA)

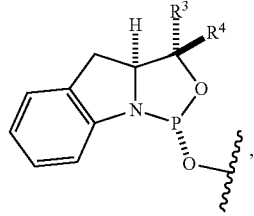
(VIIB)

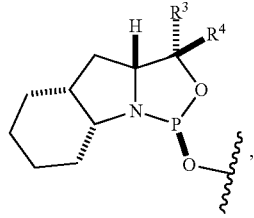
(VIIA')

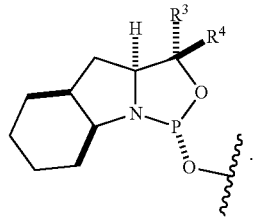
(VIIB')

wherein

═ is a single carbon-carbon bond or a double carbon-carbon bond;

each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and each of $R^3$ and $R^4$ is independently H, optionally substituted $C_{1-6}$ alkyl, or optionally substituted $C_{6-10}$ aryl.

5. The nucleoside phosphoramidite of claim 4, wherein the nucleoside phosphoramidite is of the following structure:

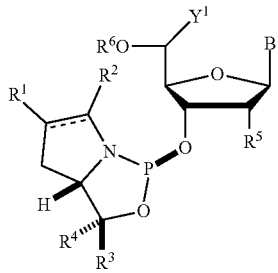
(VIA)

or

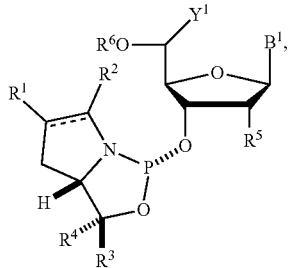
(VIB)

wherein $B^1$ is a nucleobase;

$Y^1$ is H or $C_{1-6}$ alkyl;

$R^5$ is H, O-protected hydroxyl, optionally substituted $C_{1-6}$ alkoxy, or halogen; and $R^6$ is a hydroxyl protecting group.

6. The nucleoside phosphoramidite of any one of claims 5, wherein $R^6$ is dimethoxytrityl.

7. The nucleoside phosphoramidite of claim 4, wherein $R^1$ and $R^2$, together with the atoms to which each is attached, combine to form an optionally substituted 5- to 8-membered ring.

8. The nucleoside phosphoramidite of claim 4, wherein the phosphoramidite is of the following structure:

9. A method of preparing a composition comprising an oligonucleotide comprising a stereochemically enriched internucleoside phosphorothioate, the method comprising (i) reacting the nucleoside phosphoramidite of claim 4 with a coupling activator and a nucleoside comprising a 5'-hydroxyl or an oligonucleotide comprising a 5'-hydroxyl, (ii) reacting with an electrophilic source of acyl, and (iii) reacting with a sulfurizing agent to produce the oligonucleotide comprising a stereochemically enriched internucleoside phosphorothioate triester.

10. A method of preparing the nucleoside phosphoramidite comprising a sugar bonded to a nucleobase and phosphoramidite of the following structure:

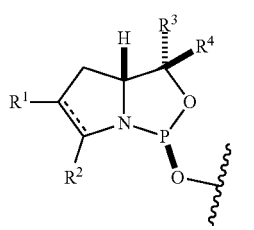
(VA)

or

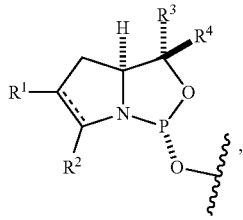
(VB)

wherein

═ is a single carbon-carbon bond or a double carbon-carbon bond;

each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring; and each of $R^3$ and $R^4$ is independently H, optionally substituted $C_{1-6}$ alkyl, or optionally substituted $C_{6-10}$ aryl;

the method comprising reacting a sugar bonded to a nucleobase with a compound of formula (VIIIA) or (VIIIB):

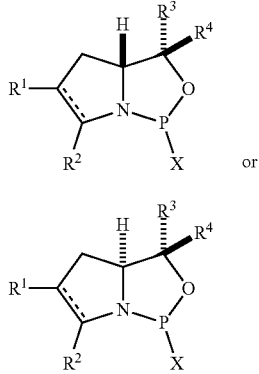
(VIIIA)

or (VIIIB)

wherein

X is a halogen or pseudohalogen.

11. An oligonucleotide comprising one or more internucleoside groups independently selected from the group consisting of linkers of formulas (XIA), (XIB), (XIIA) and (XIIB):

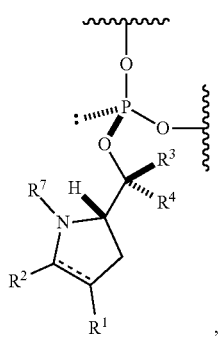
(XIA)

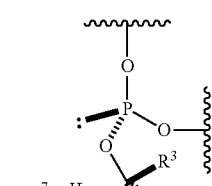
(XIB)

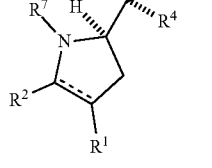
(XIIA)

, and

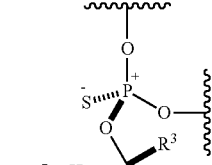
(XIIB)

where

═ is a single carbon-carbon bond or a double carbon-carbon bond;

each of $R^1$ and $R^2$ is independently an optionally substituted $C_{1-6}$ alkyl or optionally substituted $C_{6-10}$ aryl, or $R^1$ and $R^2$, together with the atoms to which each is attached, combine to form an optionally substituted 5- to 8-membered ring;

each of $R^3$ and $R^4$ is independently H, optionally substituted $C_{1-6}$ alkyl, or optionally substituted $C_{6-10}$ aryl; and $R^7$ is acyl.

12. The compound of claim 1, wherein each of $R^3$ and $R^4$ is independently H.

13. The compound of claim 2, wherein the optionally substituted 5- to 8-membered ring is an optionally substituted 6-membered carbocyclic ring.

14. The nucleoside phosphoramidite of claim 4, wherein each of $R^3$ and $R^4$ is independently H.

15. The nucleoside phosphoramidite of claim 7, wherein the optionally substituted 5- to 8-membered ring is an optionally substituted 6-membered carbocyclic ring.

16. The method of claim 10, wherein the optionally substituted 5- to 8-membered ring is an optionally substituted 6-membered carbocyclic ring.

17. The method of claim 10, wherein each of $R^3$ and $R^4$ is independently H.

18. The oligonucleotide of claim 11, wherein the substituted 5- to 8-membered ring is substituted 6-membered carbocyclic ring.

19. The oligonucleotide of claim 11, comprising one or more internucleoside groups independently selected from the group consisting of linkers of formulas (XIIA) and (XIIB):

20. The oligonucleotide of claim 11, comprising one or more internucleoside groups independently selected from the group consisting of linkers of formulas (XIA) and (XIB):

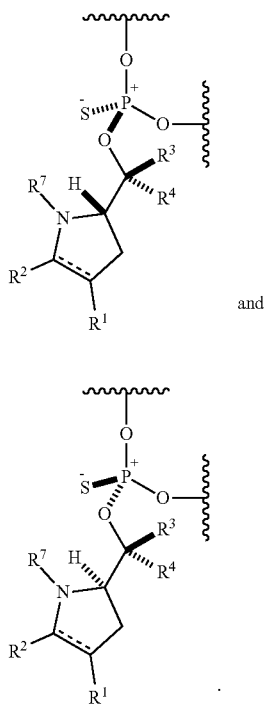

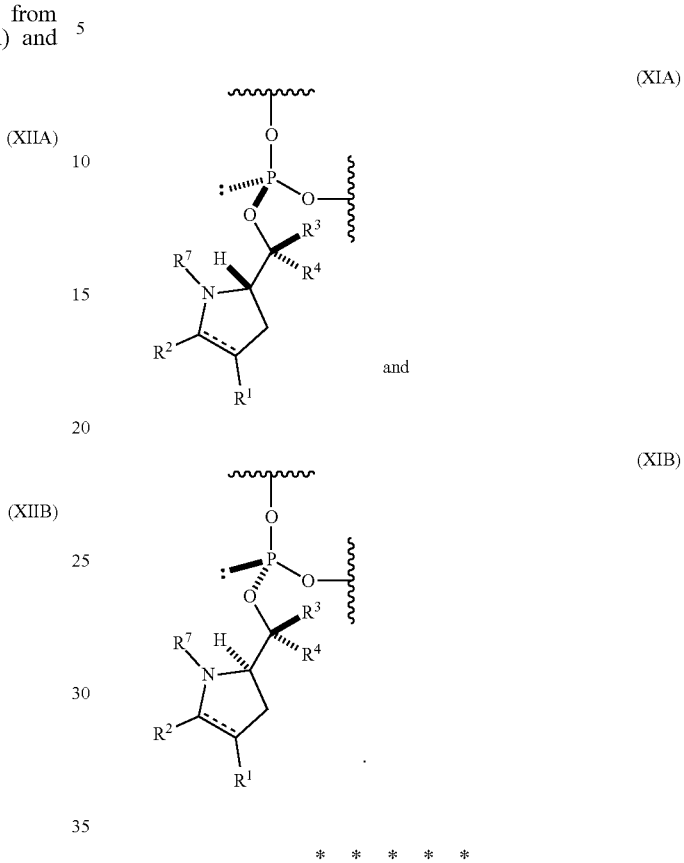

* * * * *